(12) United States Patent
Colvin et al.

(10) Patent No.: US 11,471,751 B2
(45) Date of Patent: Oct. 18, 2022

(54) SYSTEMS AND METHODS FOR PROVIDING ULTRAVIOLET STERILIZATION, DISINFECTION AND DECONTAMINATION OF GAMING MACHINES AND ASSOCIATED EQUIPMENT

(71) Applicant: Gaming Arts, LLC, Las Vegas, NV (US)

(72) Inventors: David Colvin, Las Vegas, NV (US); Eric D. Colvin, Las Vegas, NV (US)

( * ) Notice: Subject to any disclaimer, the term of this patent is extended or adjusted under 35 U.S.C. 154(b) by 0 days.

(21) Appl. No.: 17/446,430

(22) Filed: Aug. 30, 2021

(65) Prior Publication Data
US 2021/0386887 A1 Dec. 16, 2021

Related U.S. Application Data

(63) Continuation of application No. 16/909,895, filed on Jun. 23, 2020, now Pat. No. 11,344,791, which is a continuation of application No. 16/866,517, filed on May 4, 2020, now Pat. No. 10,946,110.

(60) Provisional application No. 63/012,817, filed on Apr. 20, 2020.

(51) Int. Cl.
| | |
|---|---|
| *A63F 1/12* | (2006.01) |
| *A61L 2/10* | (2006.01) |
| *A61L 2/24* | (2006.01) |
| *G07F 17/32* | (2006.01) |
| *A61L 2/26* | (2006.01) |

(52) U.S. Cl.
CPC .................. *A63F 1/12* (2013.01); *A61L 2/10* (2013.01); *A61L 2/24* (2013.01); *A61L 2/26* (2013.01); *G07F 17/3209* (2013.01); *A61L 2202/11* (2013.01); *A61L 2202/14* (2013.01); *G07F 17/3206* (2013.01); *G07F 17/3216* (2013.01)

(58) Field of Classification Search
CPC .......... A61L 2/10; A61L 2/24; A61L 2202/11; G07F 17/3209; G07F 17/3216
See application file for complete search history.

(56) References Cited

U.S. PATENT DOCUMENTS

| | | | | |
|---|---|---|---|---|
| 6,311,974 | B1 * | 11/2001 | Koga | G07F 17/32 273/118 R |
| 2009/0252646 | A1 * | 10/2009 | Holden | A61L 2/202 422/24 |
| 2021/0019719 | A1 * | 1/2021 | Kraft | G06Q 20/18 |

* cited by examiner

*Primary Examiner* — Reginald A Renwick
(74) *Attorney, Agent, or Firm* — FisherBroyles, LLP; Rob L. Phillips

(57) ABSTRACT

Systems and methods for providing ultraviolet (UV) sterilization, disinfection and decontamination of electronic gaming machines (EGMs), gaming chips, dice, playing cards, currency, TITO tickets, etc. The ultraviolet sterilization, disinfection and decontamination may include a singular or plurality of UV lamps of any type or style or UV LEDs or RGB-UV LEDs or any type or style of UV LEDs of at least such wavelengths to be effective in at least partially reducing or eliminating viruses or the like. The UV sources are mounted on, in or proximate to a variety of gaming devices or equipment such as EGMs, mechanical gaming machines, chip trays, chippers, dice holders, automatic card shufflers, bill validators, currency counting devices, currency dispensing devices, printers, magnetic card readers, playing card and currency sterilization, disinfection or decontamination storage mechanisms, ATMs, redemption machines, promotional kiosks, etc., or similar devices used in other industries.

27 Claims, 14 Drawing Sheets

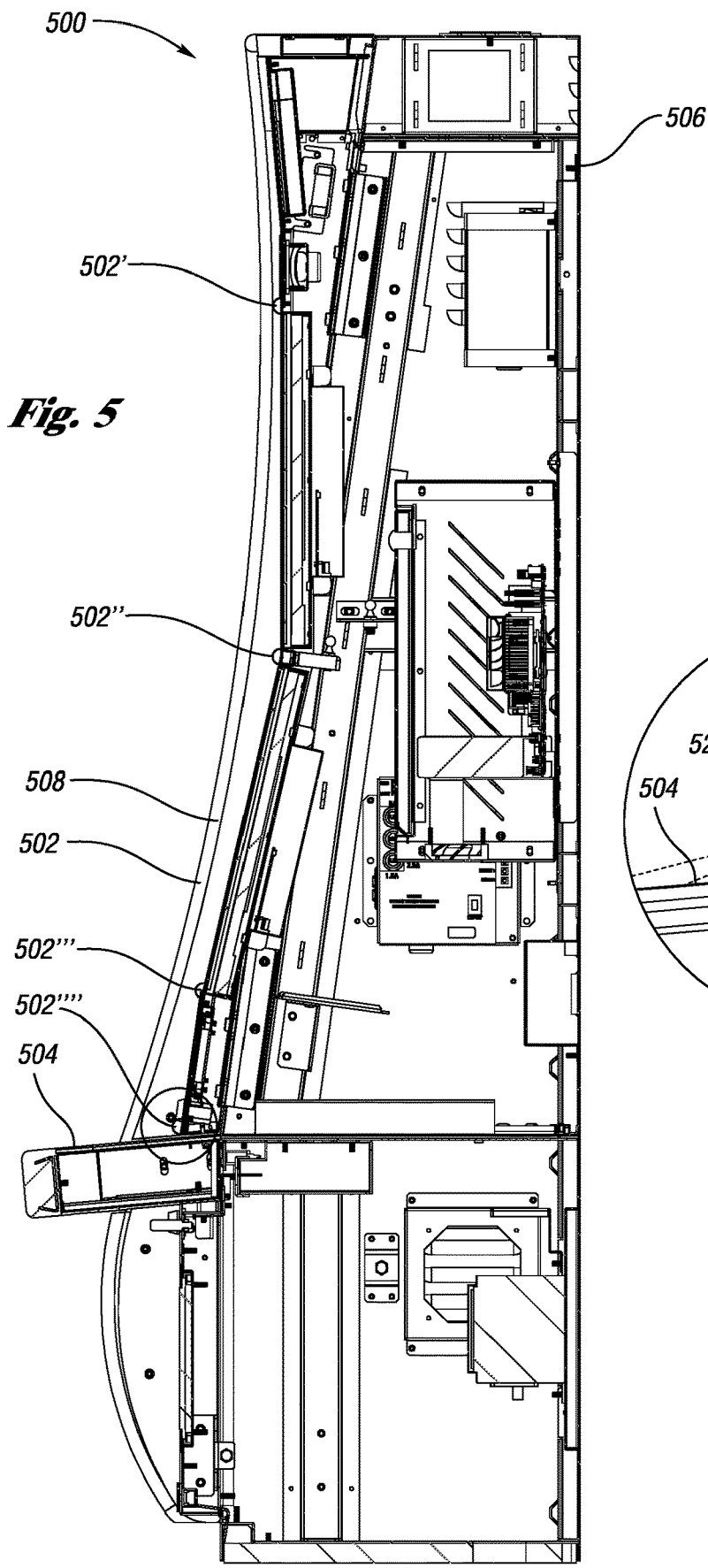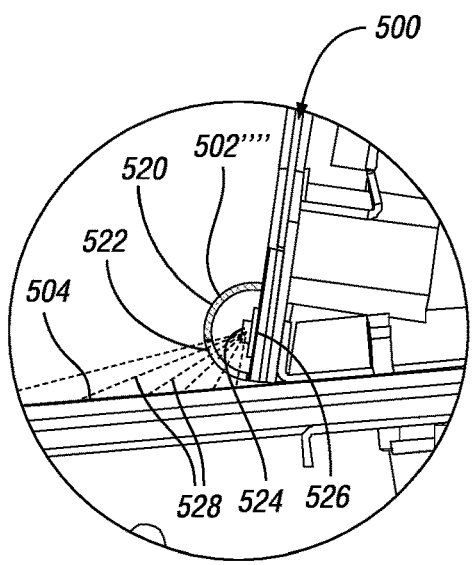
Fig. 5
Fig. 5A

SYSTEMS AND METHODS FOR PROVIDING ULTRAVIOLET STERILIZATION, DISINFECTION AND DECONTAMINATION OF GAMING MACHINES AND ASSOCIATED EQUIPMENT

CROSS-REFERENCE

This application is a continuation of U.S. patent application Ser. No. 16/909,895 filed Jun. 23, 2020 which is a continuation of U.S. patent application Ser. No. 16/866,517 filed May 4, 2020, now U.S. Pat. No. 10,946,110, which claims priority to U.S. Patent Application No. 63/012,817 filed Apr. 20, 2020 all of which are incorporated herein by reference for all purposes.

FIELD OF THE INVENTION

The embodiments of the present invention relate to systems and methods for providing ultraviolet sterilization, disinfection and decontamination of gaming machines and components, including mechanical and electronic gaming machines (EGMs) and other gaming equipment and mechanisms utilizing ultraviolet light sources. The embodiments of the present invention contemplate both retrofitting existing and legacy EGMs and other gaming equipment and mechanisms, and future EGMs and other gaming equipment and mechanisms for new installations. Embodiments include a single ultraviolet light source or a plurality of ultraviolet light sources mounted on or in the EGM or other gaming equipment and mechanisms or proximate thereto.

BACKGROUND

Casinos derive much of their gaming revenue from electronic gaming machines ("EGMs") otherwise known as slot machines, either electronic or electromechanical, and a variety of casino table games such as blackjack, roulette, craps, baccarat, etc. In the year 2020, the world is coping with a viral pandemic known as Covid-19 which has effectively caused the closure of most casinos around the globe and substantially all or all casinos and gaming establishments in North America. This closure not only extends to casinos but almost all gaming establishments including sports books, poker parlors, card rooms, bingo halls, keno lounges, etc.

SUMMARY

One skilled in the art will recognize that certain types of EGMs, generally utilized in regulated casino environments, are still commonly referred to as "slot machines." Although the etymology of the term "slot machine" was originally derived from a coin slot in the gaming machines at the time, coin slots have long since generally been replaced by payment input devices or bill validators which only accept paper currency or ticket-in-ticket-out vouchers and/or electronic fund transfer means, such as card readers, mobile device payment means, account interfaces, etc., yet EGMs are still commonly referred to as slot machines. As a result, the terms EGM and slot machine are used interchangeably and are defined to mean an electronic gaming machine entirely different than a laptop or desktop computer, cell phones, tablet computer gaming devices and the like. Although EGMs are discussed in detail, the embodiments of the present invention have similar utility for any type of gaming machine such as electronic, electromechanical or mechanical and regulated as Class II, Class III, VLT, pull tab, etc., type gaming machines.

The embodiments of the present invention provide systems and methods for providing ultraviolet sterilization, disinfection or decontamination of gaming machines and other mechanisms and objects used within a casino environment. The terms sterilization, disinfection and decontamination as used herein, include any partial or full reduction in viruses and the like and include scenarios where no sterilization, disinfection or decontamination of objects can occur but with repeated exposure to the various embodiments disclosed herein before full or partial sterilization, disinfection or decontamination does occur. The embodiments of the present invention allow for a social distancing method so that players may be physically seated at smaller distances than may be suggested by governmental authorities such as a recommended physical separation of at least six feet or 72 inches. As most gaming positions have a physical separation of approximately 28 inches between players, such as in EGM placements or table games, the only alternative without shielding or ultraviolet sterilization, disinfection and decontamination is to turn off, remove, or otherwise eliminate two out of three adjacent gaming positions to create the recommended minimum distance of 72 inches although some casino operators may close off or turn off every other machine, if allowed. This dramatic reduction in gaming positions will essentially force the closure of a great many gaming establishments as revenues will be reduced by approximately up to 70%. For example, a casino with 1,800 EGMs will need to reduce the number to 600 operable EGMs, blackjack tables with six gaming positions will need to reduce to two gaming positions, roulette tables that normally accommodate eight players will need to reduce to two gaming positions, etc. However, social distancing may not fully or even significantly reduce the risk of a virus transmission due to the many other risk factors posed within a casino environment that are not solved by social distancing. The embodiments of the present invention provide systems and methods for providing ultraviolet sterilization, disinfection and decontamination of gaming machines and associated equipment or components for mechanical and electronic gaming machines (EGMs) or casino gaming tables and objects and associated equipment that may allow gaming operators to resume to substantially normal operations. Those skilled in the art will recognize the terms light, lighting, radiate and radiation along with their variations, refer to the production of UV radiation and/or visible light.

Many players, especially in the high spend demographic, are in the 50 to 75 year-old range and have a very different perception of the Covid-19 virus compared to younger people. They have good cause for concern due to age and/or preexisting conditions. Many will be disturbed or concerned when sitting next to unknown players. The embodiments of the present invention help solve this issue and future such issues. In the current environment, one cannot underestimate the number of high spend players that will have ongoing concerns. Although younger people are less concerned, one cannot underestimate a dramatically different view from older, at risk players, who often comprise the highest player spend group. It is important to appreciate that a pandemic will stay for long periods of time, including the Covid-19 virus. Only an effective vaccine will end a pandemic which is typically at least a year or two away with current testing and approval procedures and protocols. As with many viruses, the creation of a vaccine may be elusive and take longer to develop or may not even be possible. While the current Covid-19 pandemic may subside to a large degree in 2021, if and when a vaccine is developed and distributed to the general public, it is sure not to be the last such pandemic which routinely occur in nature. One only needs to look to history to underscore the point. Most recently, the world dealt with the Zika virus in 2015 and still present, the Ebola virus of 2014-2016, the H1N1 Swine Flu pandemic of 2009 to 2010, the Aids pandemic which began in the early 1990s and continues to the present, and the Asian Flu of 1957 to 1958, just to mention the most recent. However, this is the first time in history that the world community has responded with such aggressive preventative and containment measures. It is possible that future pandemics will see similar aggressive actions which may be mitigated if certain sterilization, disinfection and decontamination measures are taken ahead of time. Such is an object of the embodiments of the present invention as it relates to the gaming industry and beyond. When people speak of flattening the infection curve, it is just that, flattening, not eliminating. As an example, while a major city may experience about 800 deaths per day at a certain point, as New York City experienced in early 2020, when the curve flattens, they may still expect 50 to 200 deaths a day for many subsequent months. The same will apply around a country and globe. Currently, as anticipated in the late spring or summer of 2020, when many casinos reopen, they will either be forced or voluntarily choose the turn off every other or two out of three gaming machines as typical slot distancing is only about 28 inches. This, every other or every third machine scenario, will most likely be more prevalent for commercial casinos subject to regulatory authorities than tribal casinos. While this may conform to social distancing guidelines and may help to alleviate player concerns and the spread of a virus, it will cause a dramatic reduction in casino revenues. While a property may reopen, it may not be profitable under this scenario or may even be forced to permanently close. Additionally, this scenario may cause issues with normal consumer traffic as there may not be enough machines on occasion or a player's favorite machine may be turned off, removed, or taken by another player and casino pits and associated table games may not reopen or if they do, only to a very limited degree.

The systems and methods herein for providing ultraviolet sterilization, disinfection and decontamination utilize ultraviolet (UV) light which falls in the range of the electromagnetic spectrum between visible light and X-rays. It has frequencies of about $8 \times 10^{14} \times 10^{16}$ cycles per second, or hertz (Hz), and wavelengths of about 400 nanometers ($1.5 \times 10^{-5}$ inches) to about 10 nm ($4 \times 10^{-7}$ inches). UV is generally divided into three sub-bands:

UVA, or near UV (315-400 nm)
UVB, or middle UV (280-315 nm)
UVC, or high UV (100-280 nm)
Far-UVC (207-222 nm)

UV radiation has enough energy to break chemical bonds. Due to their higher energies, UV photons can cause ionization, a process in which electrons break away from atoms. The resulting electron vacancy affects the chemical properties of the atoms and causes them to form or break chemical bonds that they otherwise would not. This can be useful for chemical processing, or it can be damaging to materials and living tissues. This damage can be beneficial, for instance, in disinfecting surfaces, but it can also be harmful, particularly to skin and eyes, which are most adversely affected by higher-energy UVB and certain UVC radiation. Generally, when bacteria, viruses and protozoa are exposed to adequate UV light, the UV energy destroys the genetic material (DNA) within, eliminating their ability to reproduce and cause infection. Unable to multiply, the microorganisms are "inactivated," and no longer pose a health risk. Accordingly, the proper wavelength ranges need to be selected to balance the disinfecting properties of the UV lighting while not presenting harmful effects on humans. Generally, the proper wavelengths for use with the embodiments of the present invention will fall into the far-UVC range but the shorter UVA wavelength range or even the longer UVB wavelengths may be utilized on occasion. Although perhaps not as efficient as UVC radiation in killing viruses and the like, a tradeoff exists between effectiveness and safety for humans. However, many embodiments of the present invention are designed and constructed to be operable only when humans are not present through the use of various sensors and timers or designed for use only for short periods of time when humans may be present. These embodiments are more effective and in particular, wavelengths of approximately 254 nm and 264 nm or about 207 nm to 222 nm may be very impressive at killing germs, viruses and bacteria. Fortunately, UVC radiation can pass through air without creating ozone, so UVC lamps or LEDs can be used in air to disinfect surfaces. Moreover, the UVC radiation may be shielded in order to radiate only given surfaces as opposed to surrounding areas and such use would generally be for short periods of time. Many lamp types may be used to produce UV radiation such as low-pressure or high-pressure lamps but in the case of the embodiments of the present invention, UV LEDs may be preferable due to size and adaptability to lighting effects and lighting methods used for most EGMs and small size for other gaming mechanisms or objects. In many cases, where humans may be exposed to the UV radiation, far-UVC light, with a wavelength of about 207-222 nm may be the best choice as the wavelength range has been generally proven to be safe for humans yet very effective in killing viruses and the like. Those skilled in the art will recognize that certain embodiments may utilize differing UV wavelengths depending on application, virus characteristics, human exposure factors, and effectiveness.

Those skilled in the art will recognize that casino environments may put humans at more risk than other environments. For instances, over the course of a 24-hour period, a significant number of players will play a particular EGM, potentially contaminating many surfaces on the EGM. EGMs will typically receive a very large number of cash insertions into the EGM for a large number of players, wherein some or many of the bills inserted may be contaminated, printed ticket-in-ticket-out (TITO) paper may have been handled by a number of people prior to filling an EGM printing device and may have been contaminated, numerous players cards may have been inserted into the magnetic card reader thereby potentially contaminating the magnetic card reader, etc. Similar conditions and chances of transmitting viruses also exist in a table games environment. For instance, playing cards are distributed to a significant number of different players over a period of time, including different dealers which is commonplace, any of which could contaminate one or more playing cards or even extend to automatic card shufflers and thereby pose the risk of contaminating other players or dealers.

As playing cards pose a contamination risk, so do gaming chips. In a typical table games environment, gaming chips are routinely transferred from a player to the chip tray or rack when a player loses and conversely leave the chip tray or rack when a dealer awards a payout to a winning player or exchanges them for cash buy-ins. Accordingly, a single gaming chip may often be handled by a multitude of players and dealers over a short time period. While table games utilizing playing cards pose a risk of contamination, similar risks exist on other table games that do not utilize playing cards. Table games such as craps utilize dice during play. Typically, a new player selects two dice from a plurality of dice presented by a craps dealer. Not only may the dice have already been contaminated by a previous player or "shooter" or dealer, it is commonplace for a player to kiss the dice, blow on the dice, spit on the dice, etc., for luck, posing even a greater risk of contamination.

In addition to the risks mentioned, similar contamination risks exist with cash transactions in a casino environment. Typically, cash, usually in the form of currency or even coins, circulate through a casino either from the slot floor or table games to a casino cage, ATMs, and the like. Part of the process in casinos is to drop the slot floor by emptying slot machines or pickup cash boxes from table games. Afterwards, the cash is taken to the count room for counting, accounting and/or other functions. The cash is then either deposited or returned into circulation by the casino cage, filling of ATMs, etc. Not only may the cash have been contaminated prior to a player inserting bills into an EGM or presenting to a table games dealer to obtain gaming chips, it may have already been contaminated prior to a player receiving it from a bank or other financial institution, an ATM, or the casino cage, etc. Accordingly, cash transactions pose a significant risk of contaminating players or casino staff.

Various embodiments of the present invention serve to reduce or eliminate the risk of contamination to player or casino staff through UV decontamination, disinfection and/or sterilization systems and methods. Those skilled in the art will recognize that the terms decontamination, disinfection or sterilization include only partial decontamination, disinfection or sterilization and although a goal would be to fully sterilize, disinfect or decontaminate, often only partially sterilization, disinfection or decontamination of objects used within a casino environment will be accomplished but taken as a group, any reduction of a virus spread is considered a positive advance. Moreover, as objects circulate through a casino environment, they may repeatedly pass through one or more sterilization, disinfection or decontamination stations to increase the effectiveness of the overall sterilization, disinfection and decontamination process.

Embodiments of the present invention may be independent UV generating elements, either shielded or unshielded, as in the case of EGMs or grouped together as adaptive devices for various mechanisms, such as automatic playing card shufflers, ATMs, cash counters, for example. In the case of mechanisms where cash, chips, playing cards, etc., are processed, embodiments of the present invention may be integral with the mechanisms or added to the mechanism, internally or externally, as applicable. As various objects passthrough a sterilization, disinfection and decontamination station of the base mechanism, the UV generating elements may reside on one side, two sides, three sides or all sides of a generally rectangular pass-through window within or attached to the base mechanism. Moreover, for further effectiveness, multiple sterilization, disinfection and decontamination stations may reside in or on the base mechanism. If the sterilization, disinfection or decontamination station is housed within the base mechanism with little or no exposure outside of the interior of the mechanism, higher intensity or alternate UV wavelengths may be employed.

Those skilled in the art will recognize that while UV sterilization, disinfection or decontamination methods for EGMs and various other equipment utilized in a casino environment have been described in detail, similar systems and methods also apply to bar top EGMs, and ancillary gaming equipment, such as bill validators, EGM printers, cash counting devices, card shufflers, ATMs, magnetic card readers, chip trays, chip counters or cleaners, dice trays, etc., or other similar equipment beyond the gaming industry where circumstances warrant.

Those skilled in the art will recognize that the terms approximate, approximately, about, or similar terms, when describing angles or measurements, are not intended to represent exact numbers or limit the scope as additional variations and modifications exist within the scope and spirit of the embodiments of the present invention as described. Instead they are intended as guidelines where the range may be plus or minus up to 20% of the number specified herein. For example, player tracking modules for EGMs are generally mounted on the peripheral deck either vertically or at an angle up to approximately 45° from vertical but may include angles of plus or minus 20% of the 45° specified and the vertical specified may include plus or minus 10° from vertical. Accordingly, a range of approximately 0° from vertical to 45° may be interpreted to include a range of substantially between −10° from vertical to 55° from vertical. Similarly, the terms approximate, approximately, about, or similar terms when referring to wavelengths, may include wavelengths either below or above the stated wavelength. By example, a far-UVC wavelength of about 215 nm may encompass wavelengths between 200 nm and 222 nm.

Other variations, embodiments and features of the present invention will become evident from the following detailed description, drawings and claims.

BRIEF DESCRIPTION OF THE DRAWINGS

FIG. 5 illustrates a cross section view of a conventional upright style electronic gaming machine, generally placed on a slot stand, including UV sterilization, disinfection and decontamination elements of the embodiments of the present invention;

FIG. 5A illustrates an enlarged cross section view of an upright style gaming machine including UV sterilization, disinfection and decontamination elements of the embodiments of the present invention;

DETAILED DESCRIPTION

Figure 1:
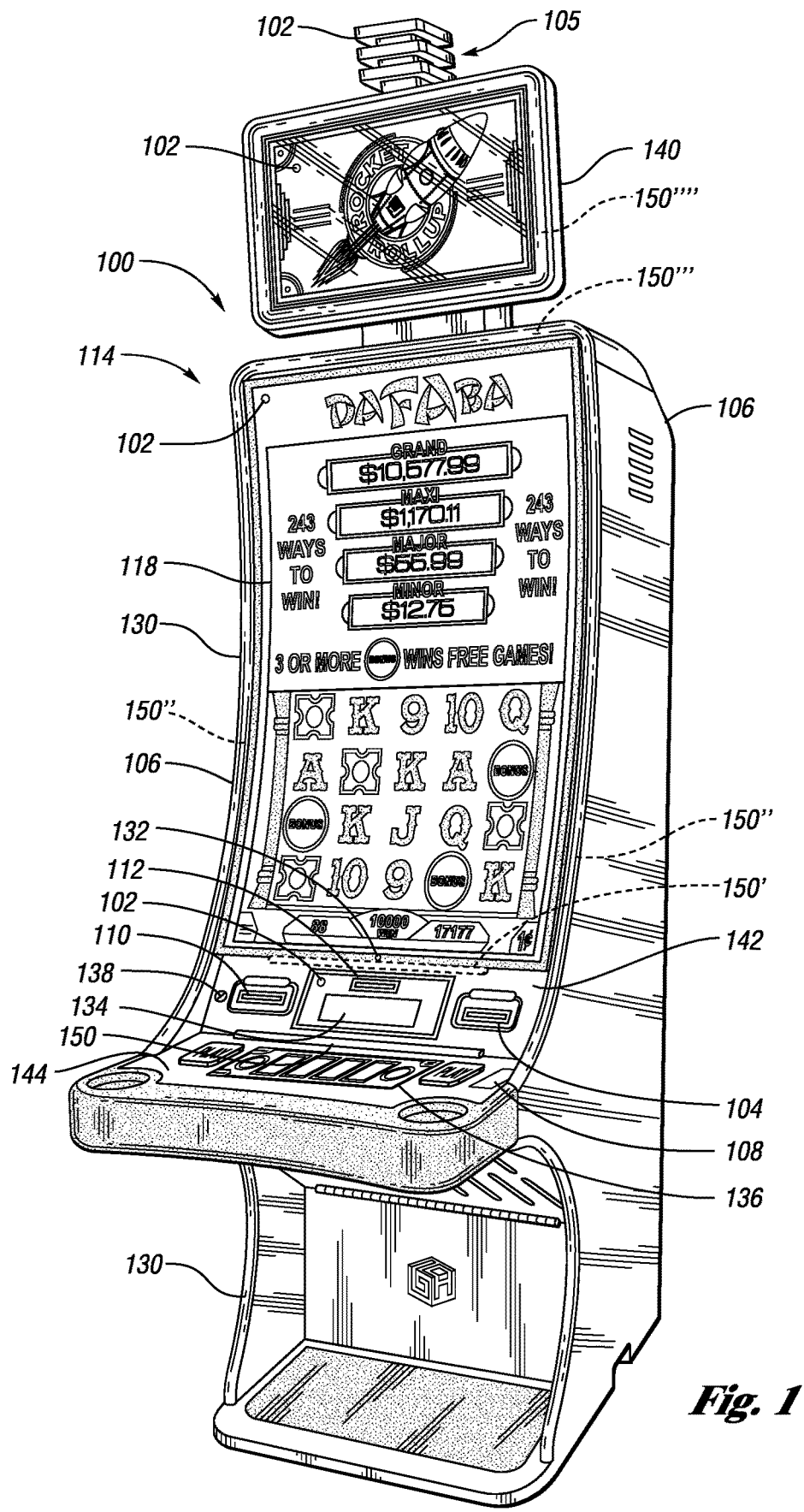
FIG. 1 illustrates a conventional floor mounted or slant type (also known as a hybrid EGM) electronic gaming machine including UV sterilization, disinfection and decontamination elements of the embodiments of the present invention.

For the purposes of promoting an understanding of the principles in accordance with the embodiments of the present invention, reference will now be made to the embodiments illustrated in the drawings and specific language will be used to describe the same. It will nevertheless be understood that no limitation of the scope of the invention is thereby intended. Any alterations and further modifications of the inventive feature illustrated herein, and any additional applications of the principles of the invention as illustrated herein, which would normally occur to one skilled in the relevant art and having possession of this disclosure, are to be considered within the scope of the invention claimed. While the present invention may be embodied in many different forms, as may be shown in the drawings and described herein in specific detail, this disclosure is to be considered as an exemplification of the principles of the invention as well as the best mode of practicing same and is not intended to limit the broad aspects or scope of the invention or claims to the specific embodiments illustrated or described.

One skilled in the art will recognize that the present invention is described below in such detail required to construct a sterilization, disinfection and decontamination mechanism of the various embodiments of the present invention.

As will be appreciated by one skilled in the art, aspects of the present invention may be embodied as a system or method.

FIG. 1 is an illustration of an exemplary electronic gaming machine (EGM) 100 that may be used with the systems and methods described herein. In one embodiment, EGM 100 is a gaming device 114. EGM 100 may include one or more comp indicators 102, which may be incorporated into, or implemented by, a candle device 105, lighting element 130, displayed on monitor 118, displayed on the player tracking module 134, displayed as an LED indicator on button panel 136 which is located on the button deck 144, or another device. One or more cameras 132 may be provided with or as part of the EGM 100 to capture images of the player or other aspects of game play. In addition to capturing images of a player or other aspects of the game, the camera 132 may be an infrared or combination infrared and normal light range camera that is able to take an infrared photo of a player and determine the body temperature of a player. If a processor determines that the temperature of a player exceeds preestablished limits, it can notify management and/or staff through the slot accounting system, can notify the player directly via a visual or audio message on the game, player tracking module display, or LCD button deck, can notify staff via a signal on the EGM candle 105, can process a signal to a player via their cell phone or a monitoring person's cell phone, or any other convenient means of notification. In this way, when an operator is notified, they may be able to ask the high temperature player to leave the premises, recommend medical attention or further evaluation, restrict the player's movement, trace the player's movements, notify other guests or players, notify the player's friends or family, or similar, The button deck of hybrid or slant type EGMs generally projects outwardly from the main cabinet and may be horizontally disposed or at slight angles from horizontal and also serves as an armrest for the play. Button decks on upright type EGMs generally project out less from the main cabinet and may not contain enough room to serve as an armrest for the player. Button decks of bar top EGMs are located below the main game screen, closer to the player, with the armrest provided by the bar top itself or bar top armrest or bar rail.

The EGM 100 includes one or more screens and may include a curved portrait mounted screen 118 although other screens or screen configuration may also be employed such as, flat screen, J-curve, reverse J-curve, S-curve multiple horizontal monitors, etc. The screen 118 may be configured to display game content to the player or any other information regarding the game, the casino, rules, pay tables, promotions, advertisements, or any multimedia content. In one embodiment, the screen 118, also referred to as a primary game display, may comprise multiple, separate displays. Additional lights 130 may be incorporated into the gaming machine to providing lighting for the player or ornamentation for the EGM 100.

A scanner 108 is provided to scan tickets which have bar or box codes, or for scanning money, cards, or any other media. In addition, scanner 108 may include other connectivity means such as blue tooth communications, near field communications or similar. Similar, a card reader 112 is provided to read one or more aspects of cards, such as player tracker or rewards cards, personal identification cards, electronic funds transfer (EFT) cards, and/or credit cards and is located on the peripheral deck 142. The EGM 100 may also include a printer 110. The printer 110 may print on any type media depending on the printer capabilities. Any type content may be printed including but not limited to cash out tickets (also known as ticket-in-ticket-out or TITO tickets or vouchers), coupons, gift certificates, comps, prizes, gaming codes, redemption codes, bar or box codes, receipts, IRS reporting documents, or any other type of information. Also, part of this embodiment is a cash acceptor 104 configured to accept paper money, ticket-in-ticket-out vouchers, or any type physical item associated with the gaming machine 100. A USB port 138 or other type charging or I/O port such as an induction charging unit is provided for phone charging or interfacing the user's phone to the gaming machine. Numerous other buttons and player interface elements are presented with the gaming machine to accept player input. The screen 118 may be configured as a touch screen.

As illustrated, the EGM 100 includes sterilization, disinfection and decontamination mechanism 150 of the embodiments of the present invention attached at the junction of the button deck 144 and peripheral deck 142 of the EGM 100. Those skilled in the art will recognize that while the sterilization, disinfection and decontamination mechanism 150 is shown at the junction of the button deck and peripheral deck, this is but one location that will serve the purpose of the embodiments of the present invention. As used herein "sterilization, disinfection and decontamination mechanism" may include one or more active members (e.g., UV LEDs). Many alternative locations exist for one or a plurality of sterilization, disinfection and decontamination mechanisms. Such mechanisms may even be built into the conventional LED lighting strips 130 wherein two separate LED strips, one a RGB LED strip and the other a UV LED strip, are included within the LED lens or cover or every other LED may be a RGB LED alternating with UV LEDS, or similar. Alternate locations of the sterilization, disinfection and decontamination mechanisms of the embodiments of the present invention are shown in locations, 150', 150'', 150''' and 150'''', and 150'''''. These locations may be independent or part of a plurality of sterilization, disinfection and decontamination mechanisms operating together. Similar alternate locations exist for all of the various embodiments of the present invention. The only true limitation associated with locating the sterilization, disinfection and decontamination mechanisms is the ability of the radiated UV light to reduce the virus, bacteria or similar life form that it is intended to control. Those ordinarily skilled in the art will recognize that the LED lighting strips 130 may be flush with the surface of the EGM 100, may be raised above the surface of the EGM 100, may be in the form of edge lit lighting panels attached to the EGM 100, etc. In addition, several locations may serve not only to allow for convenient attachment to the EGM 100 but at the same time shield the UV radiation from direct exposure to the player. Such locations may also allow for increased UV intensity, if desired. For instance, UV location 150' may attach to the EGM 100 display 118. If the UV lighting is located on the exterior bezel of display 118, it will allow for direct exposure to not only portions of the EGM 100 but to the player as well. Alternatively, the UV location may be mounted on the bottom face of the display 118 housing whereas the UV radiation will be generally directed downwardly and be generally directed onto the button deck 144 and peripheral deck 118. However, as illustrated, display 118 is raised or floats above a support structure which allows for the UV location 150' to be located on the underside of display 118 or the bottom face of a recessed display support structure, where the lower edge portion of display 118 will shield UV location 150' allowing exposure to the button deck and peripheral devices but not or at least limited direct exposure to the player generally beyond their arms and hands. Of course, the angularity of the non-shielded UV lighting will be governed by the geometric relationship between location 150' and the display 118.

Figure 2:
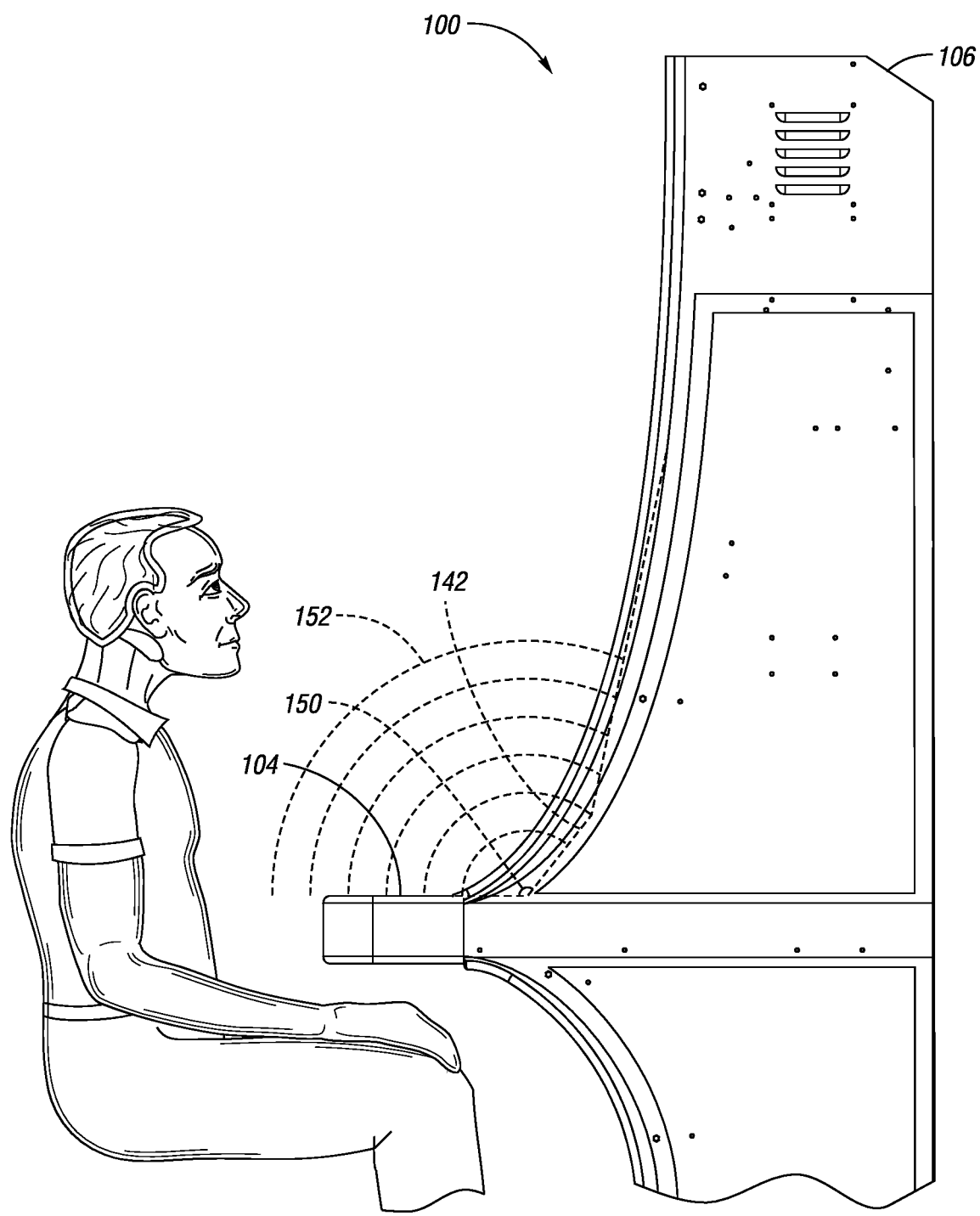
FIG. 2 illustrates a side view of a conventional slant style electronic gaming machine, normally placed on the casino floor, including UV sterilization, disinfection and decontamination elements of the embodiments of the present invention.

FIG. 2 illustrates an elevational side view of a conventional slant style electronic gaming machine 100 including the EGM cabinet 106 and sterilization, disinfection and decontamination mechanism 150 of the embodiments of the present invention. As illustrated, the sterilization, disinfection and decontamination mechanism 150 of the embodiments of the present invention is located at the junction of the button deck and peripheral deck. The UV radiation radiates from the sterilization, disinfection and decontamination mechanism 150 of the embodiments of the present invention and is illustrated as curved broken lines 152. As illustrated in FIG. 1, many different locations may exist for the sterilization, disinfection and decontamination mechanism 150 of the embodiments of the present invention.

Figure 3:
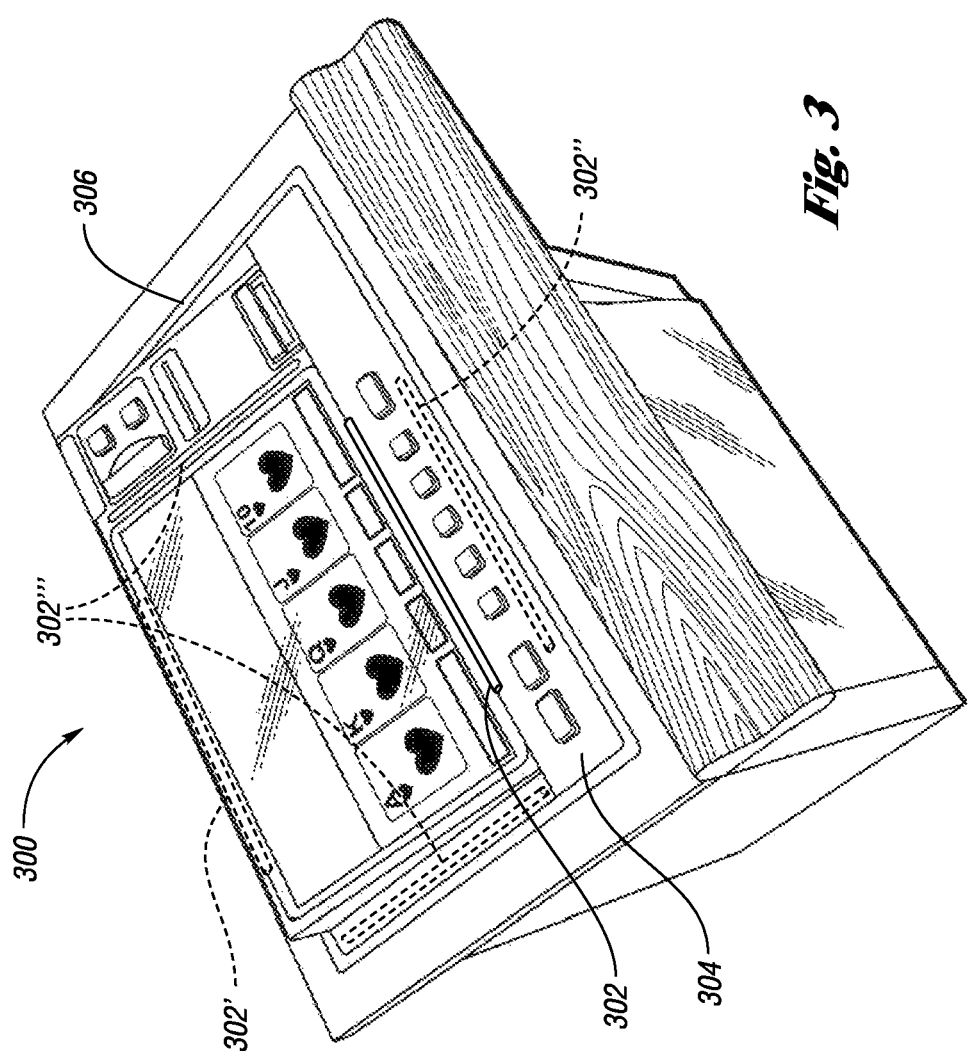
FIG. 3 illustrates a conventional bar top type electronic gaming machine including UV sterilization, disinfection and decontamination elements of the embodiments of the present invention.

FIG. 3 illustrates a conventional bar top type electronic gaming machine 300 including the EGM cabinet 306 and sterilization, disinfection and decontamination mechanism 302 of the embodiments of the present invention. As illustrated, the sterilization, disinfection and decontamination mechanism 302 of the embodiments of the present invention is located on the button deck 304. Many different locations may exist for the sterilization, disinfection and decontamination mechanism 302 of the embodiments of the present invention as shown in locations 302', 302" and 302'". Either a single sterilization, disinfection and decontamination mechanism may be utilized or a plurality of sterilization, disinfection and decontamination mechanisms may also be employed as shown with sterilization and decontamination mechanism 302'".

Figure 4:
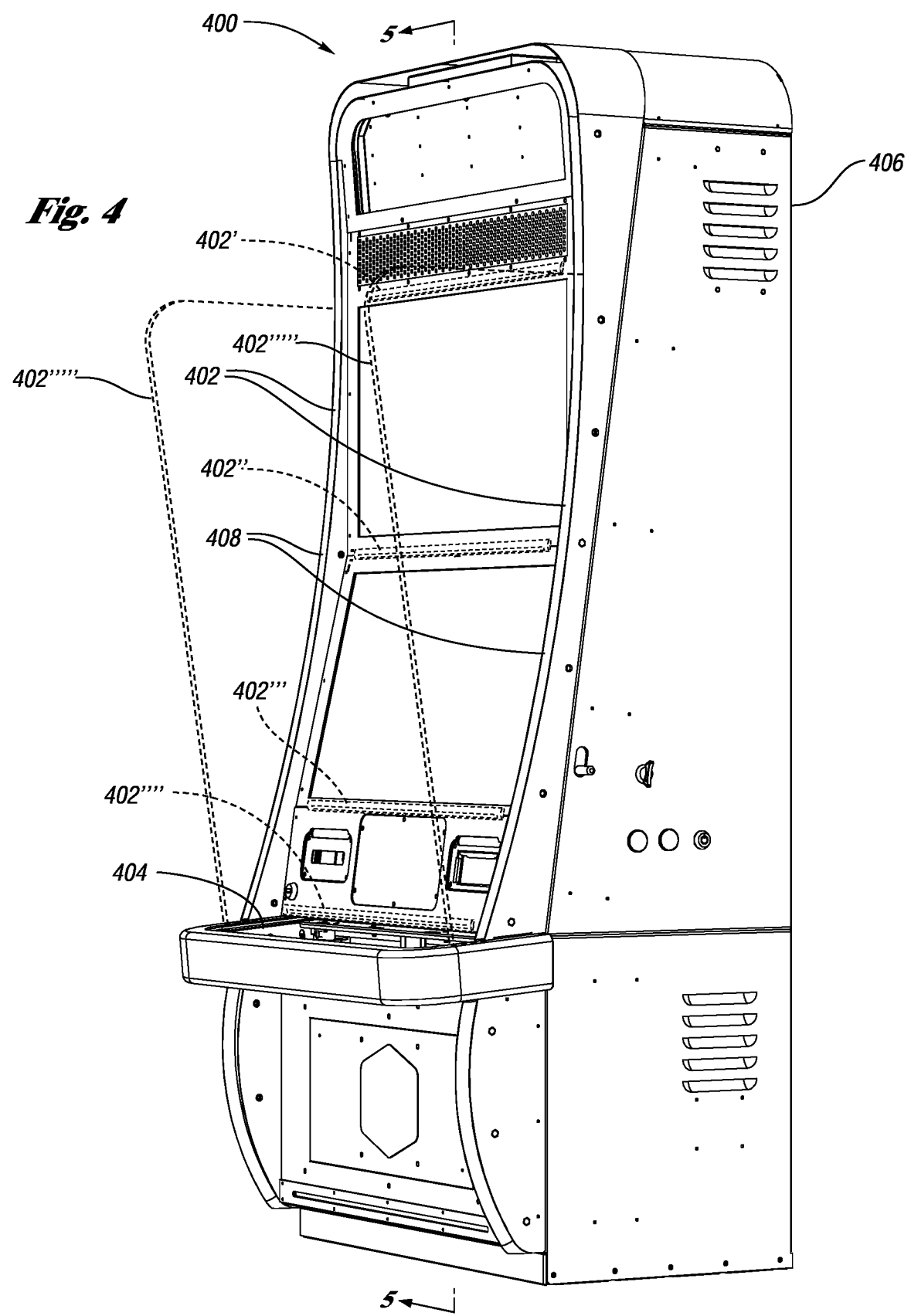
FIG. 4 illustrates a side elevational view of a conventional upright style electronic gaming machine, normally placed on a slot stand, including UV sterilization, disinfection and decontamination elements of the embodiments of the present invention.

FIG. 4 illustrates a side perspective view of a conventional upright style gaming machine 400. The conventional upright gaming 400 machine includes cabinet 406 and button deck 404. The sterilization, disinfection and decontamination mechanism 402 in this embodiment exists within the decorative LED lighting strips 408 but may be located in any convenient and effective location such as 402', 402", 402'", 402"", 402'"", or other location. Shown in phantom lines are edge lit side panels 402'"" to which the sterilization, disinfection and decontamination mechanism 402 may be attached. Those ordinarily skilled in the art will recognize that the LED lighting strips 400 may be flush with the surface of the EGM 400, may be raised above the surface of the EGM 100, may be in the form of edge lit lighting panels 402'"" attached to the EGM 400, etc.

FIG. 5 illustrates a cross section view of an upright style gaming machine 500. The conventional upright gaming 500 machine includes cabinet 506 and button deck 504. The sterilization, disinfection and decontamination mechanism 502 in this embodiment is part of the decorative LED lighting strips 508 but may be located in any convenient and effective location such as 502', 502", 502'", 502"" or other location.

Figure 6:
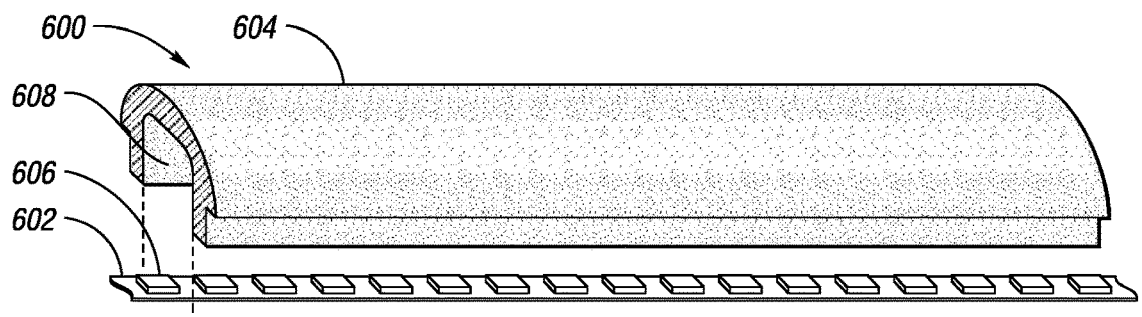
FIG. 6 illustrates an exploded perspective view of prior art decorative RGB LED strip lighting used on gaming machines along with a translucent cover or lens.

FIG. 5A illustrates an enlarged cross section view of an upright style gaming machine 500. As previously described, the sterilization, disinfection and decontamination mechanism 502 may be located in any convenient location on the gaming machine 500 such as that illustrated. In any embodiment of the present invention, it may be desirable to shield the UV radiation to minimize potential detrimental effects to humans, whether real or imagined. As shown, sterilization, disinfection and decontamination mechanism 502 includes a shielding housing member 520 that at least partially encloses a UV strip 526 and UV light source 524. Passage 522 in the sterilization, disinfection and decontamination mechanism 502 allows for the UV radiation to escape from the sterilization, disinfection and decontamination mechanism 502 and radiate the top of the button deck 504, thereby sterilizing, disinfecting and decontaminating the button deck surface, buttons, and other features on the button deck 504 as illustrated by schematic radiation lines 528. Passage 522 may be an open passage, a clear lens, a translucent lens, or similar. As illustrated, the radiation is largely unable to reach the player due to the shielding mechanism 520 which largely prohibits direct radiation beyond the button deck 504. UV light source 524 may be a single or a plurality of UV light sources such as UV LEDs or other type UV light sources. In any embodiment of the present invention, it may be desirable to also include RGB or similar LED lighting to enhance the aesthetics of the gaming machine 500. Such aesthetics can also be obtained by use of a combination RGB-UV LED or alternating RGB and UV LEDs. Typically, for this or any embodiment of the present invention, it may be desirable to utilize addressable LEDs to enhance lighting effects or moderate the UV radiation, whether they be separate LEDs or combination RGB-UV LEDs. [0055] FIG. 6 illustrates an exploded cross section perspective view of prior art decorative RGB LED strip lighting assembly 600 used on gaming machines including a RGB LED light strip 602 along with a translucent cover or lens 604. As illustrated, the RGB light strip 602 includes a plurality of individual RGB LEDs 606 which are received within a channel 608 defined by the translucent cover or lens 604.

Figure 7:
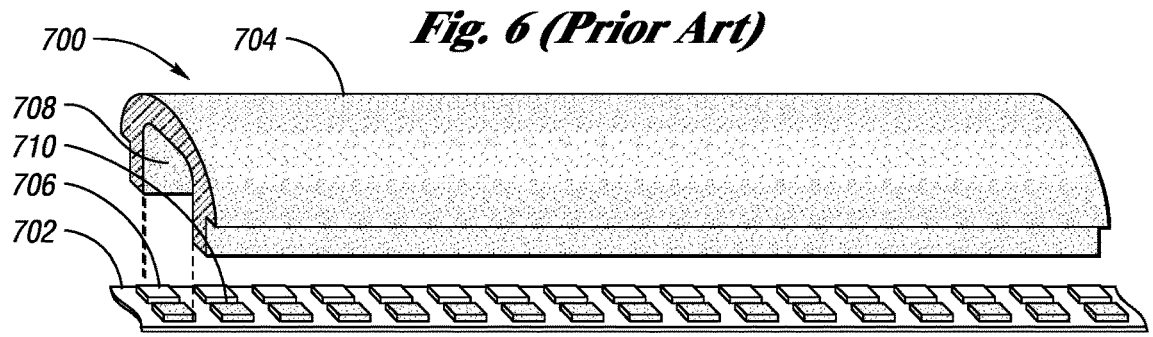
FIG. 7 illustrates an exploded perspective view of decorative RGB LED strip lighting plus an UV LED strip used together on gaming machines along with a translucent cover or lens to provide sterilization, disinfection and decontamination elements of the embodiments of the present invention.

FIG. 7 illustrates an exploded cross section perspective view of decorative RGB-UV LED strip lighting assembly 700 used on gaming machines including a RGB-UV LED light strip 702 along with a translucent cover or lens 704. As illustrated, the RGB-UV light strip 702 includes a plurality of individual RGB LEDs 706 and a plurality of UV LEDs 710 which are received within a channel 708 defined by the translucent cover or lens 704. Although shown on common strip 702, the plurality of RGB LEDs 706 may reside on a first strip and the UV LEDs 710 may reside on a second separate strip. As used throughout this disclosure, the LEDs may be addressable or non-addressable.

Figure 8:
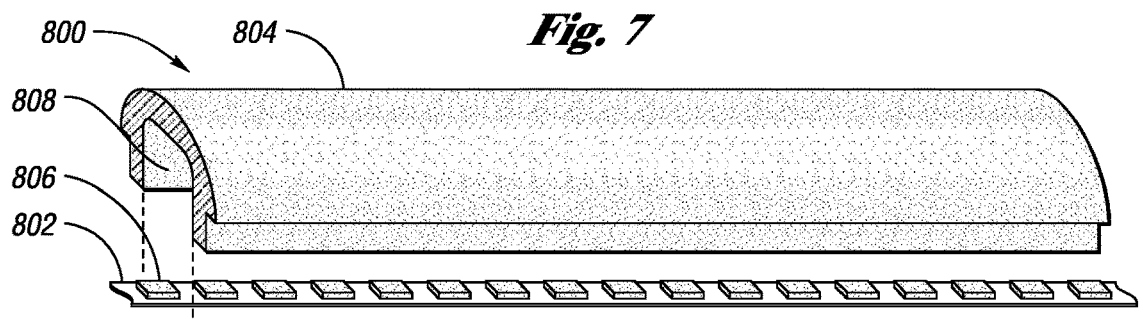
FIG. 8 illustrates an exploded perspective view of UV LED strip used on gaming machines along with a translucent cover or lens to provide sterilization, disinfection and decontamination elements of the embodiments of the present invention.

FIG. 8 illustrates an exploded cross section perspective view of another embodiment of a decorative UV LED strip assembly 800 used on gaming machines including a UV LED strip 802 along with a translucent cover or lens 804. As illustrated, the UV light strip 802 includes a plurality of individual UV LEDs 806 received within a channel 808 defined by the translucent cover or lens 804.

Figure 9:
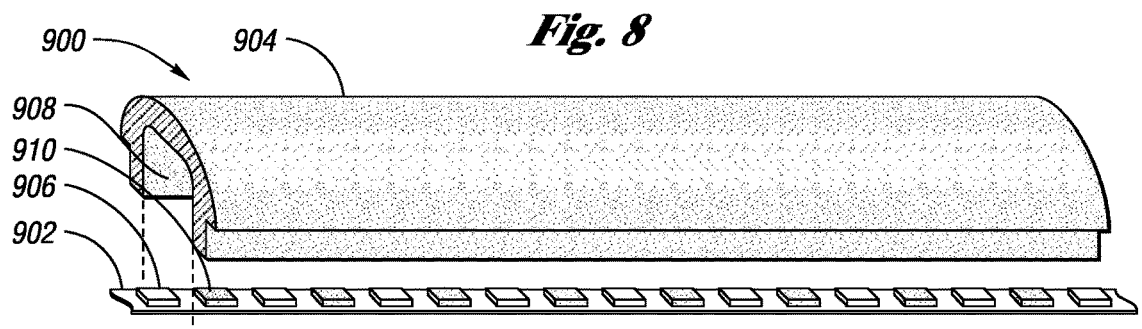
FIG. 9 illustrates an exploded perspective view of decorative RGB LED lighting used on gaming machines including alternating UV LED along with a translucent cover or lens to provide sterilization, disinfection and decontamination elements of the embodiments of the present invention.

FIG. 9 illustrates an exploded cross section perspective view of another embodiment of a decorative RGB-UV LED strip lighting assembly 900 used on gaming machines including a RGB-UV LED light strip 902 along with a translucent cover or lens 904. As illustrated, the RGB-UV LED light strip 902 includes a plurality of individual RGB LEDs 906 and a plurality of UV LEDs 910 which alternate on the RGB-UV LED strip 902 which is received within a channel 908 defined by the translucent cover or lens 904. Those skilled in the art will recognize that any convenient alternating spacing may be utilized such as every other LED is an UV LED, every third LED is an UV LED, or any similar alternating or spacing arrangement.

Figure 10:
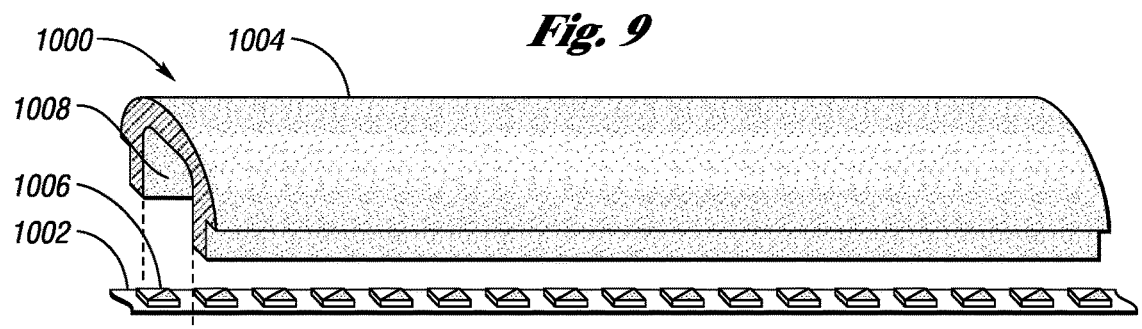
FIG. 10 illustrates an exploded perspective view of hybrid RGB-UV LED lighting used on gaming machines along with a translucent cover or lens to provide sterilization, disinfection and decontamination elements of the embodiments of the present invention.

FIG. 10 illustrates an exploded cross section perspective view of another embodiment of a decorative RGB-UV LED strip assembly 1000 used on gaming machines including a RGB-UV LED strip 1002 along with a translucent cover or lens 1004. As illustrated, the RGB-UV LED light strip 1002 includes a plurality of individual RGB-UV LEDs 1006 received within a channel 1008 defined by the translucent cover or lens 1004. One aspect of the embodiments of the present invention is the combining of a plurality of LEDs into one multi-wavelength RGB-UV LED.

Figure 11:
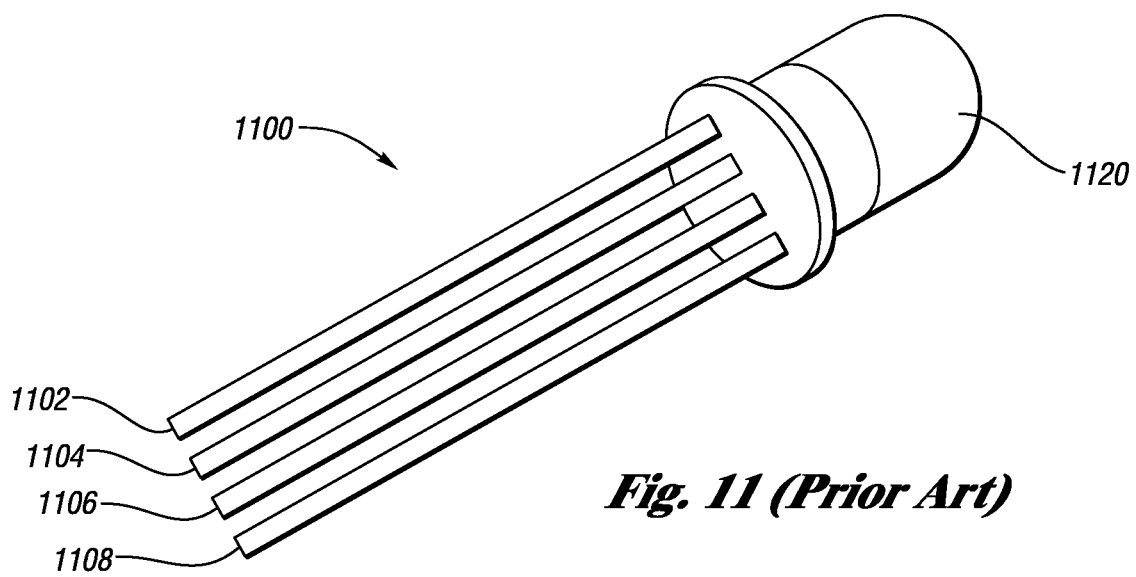
FIG. 11 illustrates a simplified perspective view of a prior art RGB LED including four pins.

FIG. 11 illustrates a simplified perspective view of a prior art RGB LED 1100 including four pins 1102, 1104, 1106 including one common pin 1108. As shown, pin 1102 is attached to a red LED, pin 1104 is attached to a green LED and pin 1106 is attached to a blue LED. Those skilled in the art will recognize that the sequence of pins can follow any order. Moreover, those skilled in the art will recognize that if two or more individual LED are always energized simultaneously in any embodiment, two or more of the separate pins may be combined into a second common pin. The various internal components of the RGB LED are then encapsulated within housing 1120. In addition, those skilled in the art will recognize that although a simplified view of a representative LED is illustrated, LEDs of the embodiments of the present invention may be fabricated in a very large variety of sizes and shapes which are known in LED manufacturing industries.

Figure 12:
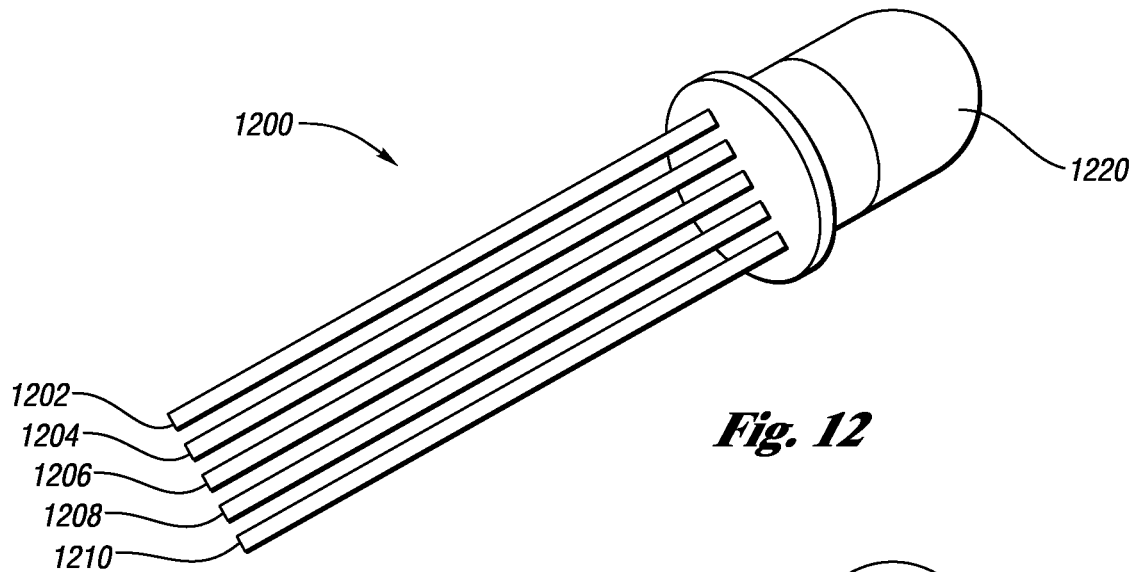
FIG. 12 illustrates a simplified perspective view one embodiment of the present invention including five pins capable of producing RGB-UV LED lighting including the production of UV radiation.

FIG. 12 illustrates a simplified perspective view of an embodiment of the present invention which is a RGB-UV LED. The RGB-UV LED 1200 includes five pins 1202,

1204, 1206, and 1208 along with one common pin 1210. As shown, pin 1202 is attached to a red LED, pin 1204 is attached to a green LED, pin 1206 is attached to a blue LED, and pin 1208 is attached to a UV LED. Those skilled in the art will recognize that the sequence of pins can follow any order. Moreover, those skilled in the art will recognize that if two or more individual LED are always energized simultaneously in any embodiment, two or more of the separate pins may be combined into a second common pin. The various internal components of the RGB LED are then encapsulated within housing 1220. In addition, those skilled in the art will recognize that although a simplified view of a representative LED is illustrated, LEDs of the embodiments of the present invention may be fabricated in a very large variety of sizes and shapes which are known in the LED manufacturing industries.

Figure 13:
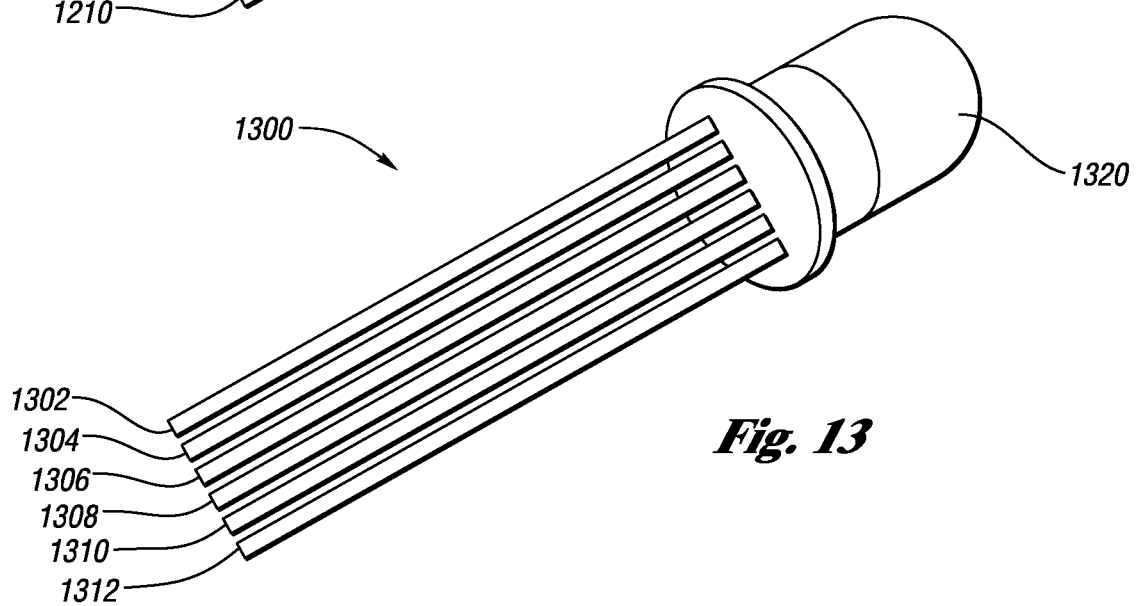
FIG. 13 illustrates a simplified perspective view one embodiment of the present invention including six pins capable of producing RGB-UV LED lighting including the production of UV radiation.

FIG. 13 illustrates a simplified perspective view of another embodiment of the present invention which is a RGB-UV LED with multiple wavelength UV LEDs. The RGB-UV LED 1300 includes six pins 1302, 1304, 1306, 1308, and 1310 along with one common pin 1312. Although this embodiment illustrates a RGB-UV LED with two separate UV wavelength LEDs, any number of differing wavelengths UV LEDs may be incorporated into the embodiments of the present invention. As shown pin 1302 is attached to a red LED, pin 1304 is attached to a green LED, pin 1306 is attached to a blue LED, pin 1308 in attached to one wavelength UV LED, and pin 1310 is attached to a different wavelength UV LED. Those skilled in the art will recognize that the sequence of pins can follow any order. Those skilled in the art will recognize that if two or more individual LED are always energized simultaneously in any embodiment, two or more of the separate pins may be combined into a second common pin. The various internal components of the RGB LED are then encapsulated within housing 1320. In addition, those skilled in the art will recognize that although a simplified view of a representative LED is illustrated, LEDs of the embodiments of the present invention may be fabricated in a very large variety of sizes and shapes which are known in the LED manufacturing industries. Those skilled in the art will recognize that in addition to the embodiments of FIG. 12 and FIG. 13, white LEDs can also be combined in a similar manner with one or more UV LEDs.

As set forth above, the strip lighting assemblies may be integral with a newly manufactured EGM or may be installed as a retrofit. When installed as a retrofit there are numerous methods for attaching the strip lighting assemblies. A first method involves replacing existing EGM lighting with the desired UV strip lighting assemblies including the UV radiation sources. With such a method, the existing translucent cover or lens (see, FIG. 6) is removed, and the existing EGM lighting is replaced with desired UV strip or RGB-UV strip lighting assemblies or one or more UV LED strip lighting assemblies may be installed adjacent to the existing EGM lighting. Alternatively, the desired UV strip lighting assemblies may be installed without accessing the existing EGM lighting. For example, the UV strip lighting assemblies may be adhered to the EGM using adhesive backing (or other means such as mechanical fasteners, extensions and/or hook and loop type fasteners commonly sold under the Velcro® brand) and then covered with a translucent cover or lens. In one embodiment, the UV strip lighting assemblies include the integral translucent cover and simply need to be adhered to the EGM and connected to a power source. The power source may be separate from the EGM or integral therewith. Those skilled in the art will recognize that the UV strip lighting assemblies may be attached to hardware which is then attached to the EGM. In other words, the UV light assemblies need not be attached to the EGM directly but may utilize intermediary hardware components such as the side panels shown in FIG. 4.

With these retrofit embodiments, it is a relatively simple task to position the UV strip lighting assemblies to radiate near the button deck, touch-screen display, bill validator, card reader and other peripherals associated with the EGM. Advantageously, lighting on EGMs is common such that the additional UV strip lighting assemblies can be positioned to blend in and interact with existing decorative EGM lighting so as not to unnecessarily raise player concerns or take away from the overall design of the EGM. The retrofit systems may be permanent or used as an interim solution until the EGMs may be completely overhauled to incorporate an integral UV lighting system.

In one embodiment, the UV strip lighting assemblies are passive in nature such that they are constantly in an on state. In another embodiment, the UV strip lighting assemblies may intermittently cycle between an on state and an off state to control the amount of UV radiation received by the player. In another embodiment, the UV strip lighting is in an on state while no player is playing the EGM and in an off state when the EGM is being played. It is also conceivable that the state of the UV strip lighting assemblies may be premised on the EGM state of multiple adjacent EGMs or a bank of EGMs. In one embodiment, for example, when three neighboring EGMs are inactive, their respective UV strip lighting assemblies are in the on state whereas if any one of the three EGMs is being played, each of the respective UV strip lighting assemblies is in an off state. Such UV strip lighting may also be addressable by the processor to control function.

Regardless of the state operation of the UV strip lighting assemblies, the UV strip lighting assemblies may or may not be connected to the electronics of the EGM. In a first embodiment, the UV strip lighting assemblies may be controlled by the EGM's processor or other internal electronics. This is true for newly manufactured EGMs or more in-depth retrofits. With such an embodiment, the EGM state (i.e., being played or idle), determined by an inserted player card or operation of a play button, dictates the operation of the UV strip lighting assemblies. Alternatively, the UV strip lighting assemblies may be controlled by their own independent controller or processor. In one such embodiment, a sensor or similar article associated with the UV strip lighting assemblies is positioned to determine the EGM state. The sensor output thus dictates the state of the UV strip lighting assemblies. The processor or controller may be programmed to control the UV light source in any manner conceivable to kill the virus and protect the player from UV radiation. In one embodiment, a central processor (e.g., server) controls the UV light source for a plurality of EGMs to which it communicates.

In one embodiment, the UV strip lighting assemblies include UV LEDs of different strengths whereby less potent UV LEDs are in an on state when the EGM is being played and the more potent UV LEDs are only in an on state when the EGM is not being played.

To further protect players from any side effects associated with UV radiation exposure, the UV strip lighting assemblies may be outfitted with reflectors, deflectors and/or directors to focus or direct the UV radiation at the specific desired point of contact with the EGM such as the touch-screen display or button deck of the EGM which contains the various player inputs (e.g., play button, cash out button, etc.). In this manner, the UV radiation is not being unnecessarily transmitted into contact with the player.

In one embodiment, multiple EGMs or a bank of EGMs may share a common arrangement of UV strip lighting assemblies or other UV light sources. For example, a bank of EGMs may utilize a common arrangement of UV light sources hanging from signage associated with the bank of EGMs or otherwise positioned above the EGMs forming the bank. In one embodiment, the common arrangement of UV light sources may be raised and lowered relative to the bank of EGMs. The state of the common arrangement of UV light sources may be controlled in the same manner as detailed above. In one embodiment, different portions of the common arrangement of UV light sources may be in different states simultaneously. Those skilled in the art will recognize that any of the previously described functions or functionality may exist for either retrofit applications, new machine installations, or any combination thereof.

Figure 14:
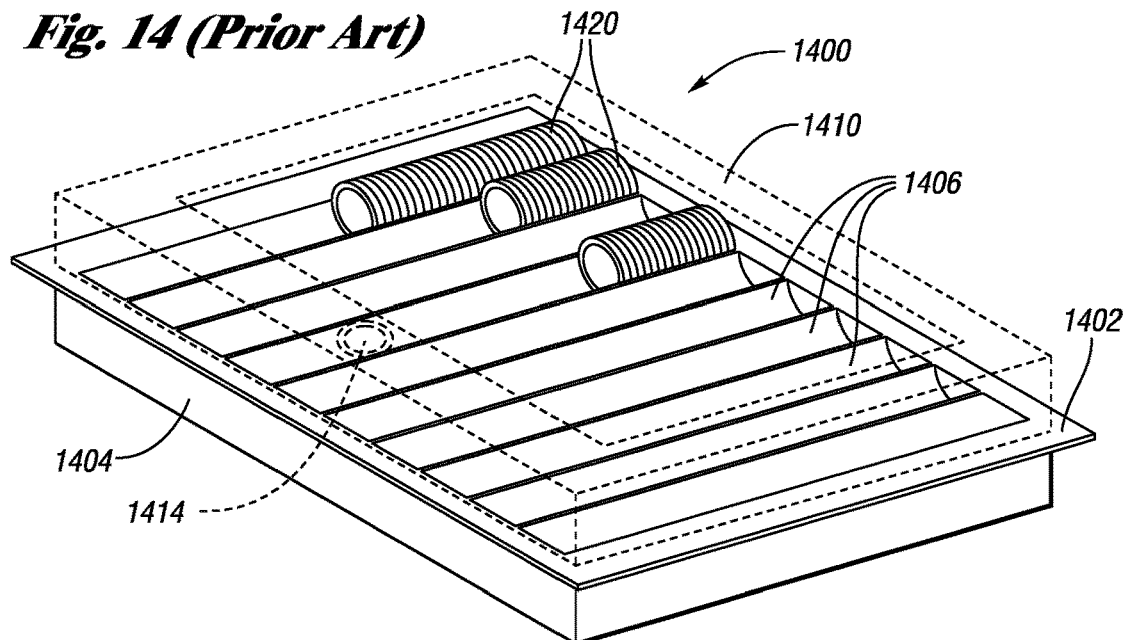
FIG. 14 illustrates a prior art chip tray that is commonplace on casino table games.

FIG. 14 illustrates an isometric view of a prior art gaming chip tray which are commonplace in the table games or "pit" section of casinos. As illustrated, gaming chip tray 1400 is generally rectangular in shape and often includes a flange 1402 which seats on the gaming table once the lower section 1404 is lowered into place. Gaming chip tray 1400 also includes a plurality of semi-circular profile recesses 1406 constructed to receive a plurality of gaming chips 1420. Also shown in broken line is the gaming chip tray cover 1410 which generally contains a lock 1414 to safeguard the gaming chips 1420 when a gaming table is not in use.

Figure 15:
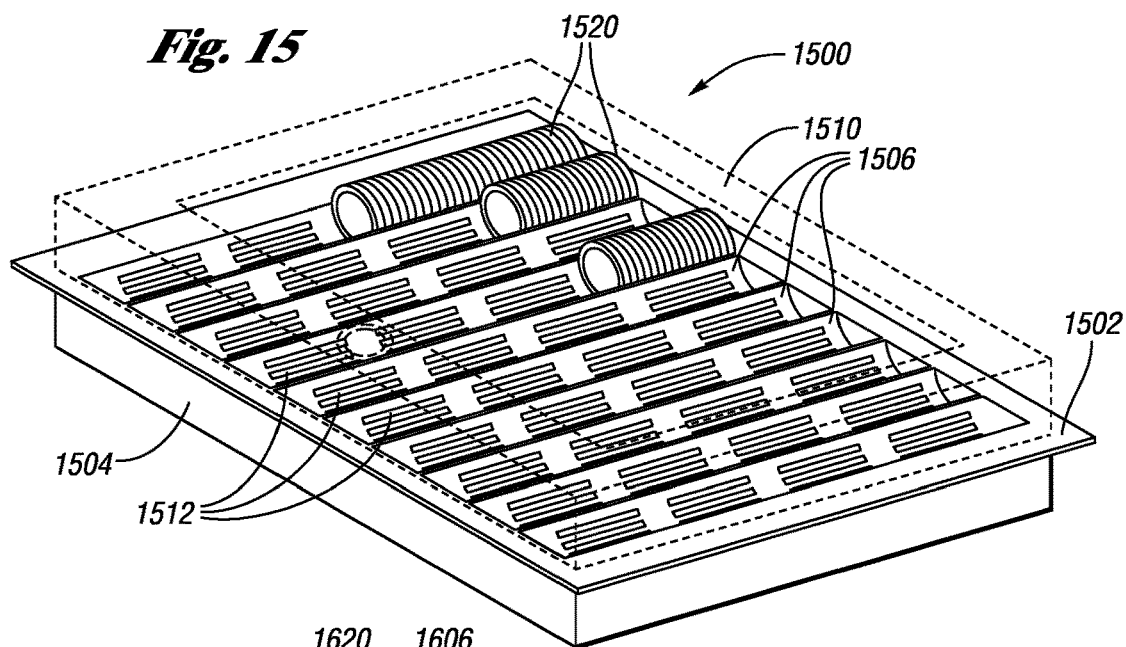
FIG. 15 illustrates a chip tray of the embodiments of the present invention which sterilizes, disinfects and decontaminates gaming chips while in use in a casino.

FIG. 15 illustrates an isometric view of gaming chip tray embodiment of the present invention. As illustrated, gaming chip tray 1500 is generally rectangular in shape and often includes a flange 1502 which seats on the gaming table once the lower section 1504 is lowered into place. Gaming chip tray 1500 includes a plurality of semi-circular profile recesses 1506 constructed to receive a plurality of gaming chips 1520. Also shown in broken line is the gaming chip tray cover 1510 which generally contains a lock 1514 to safeguard the gaming chips when a gaming table is not in use. As illustrated gaming chip tray 1500 includes a plurality of semi-circular profile recesses 1506 constructed to receive a plurality of gaming chips 1520 and within each of the plurality of semi-circular profile recesses 1506 is a plurality of openings 1512 that allow for the transmission of light or radiation to pass through from under the top portion of the gaming chip tray 1500. The plurality of openings 1512 may be open, may be transparent, may be translucent or similar. Those skilled in the art will recognize that the openings 1512 can be of many shapes as long as they provide a means of transmission. In addition, some materials may allow for the passage of UV radiation and as such, no openings may be required as long as the UV radiation can reach the gaming chips. During use, gaming chip tray 1500 will be filled with a variety of differing denomination gaming chips such as $1 chips, $5 chips, $25 chips, $100 chips, etc., arranged for easy counting in the event a dealer must pay a player once they have won a wager. As the table game progresses, the gaming chips routinely go out and then come back for placement in the gaming chip tray 1500 depending on the outcomes of wagering activities. Accordingly, the chips 1520 will be exposed to the UV radiation to the extent necessary to reduce or eliminate contamination form viruses and the like. Those familiar with the art will recognize that while the contamination of the gaming chips 1520 may only be slightly reduced or even not reduced on a particular placement, the repeated placement and replacement into the gaming chip tray 1500 may be additive to the overall decontamination of the gaming chips 1520. This repeated exposure of objects may occur in many embodiments of the present invention. Those skilled in the art will recognize that the embodiment illustrated is representative of many chip holding and handling devices such as roulette chippers, chip cleaners, and the like.

Figure 16:
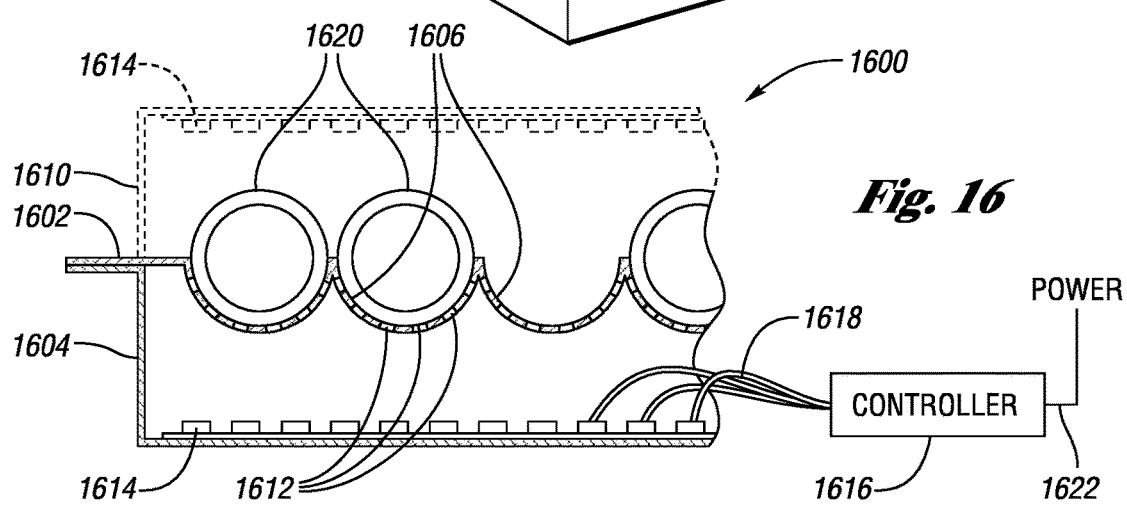
FIG. 16 illustrates a cross section of the chip tray of the embodiments of the present invention illustrated in FIG. 15 which sterilizes, disinfects and decontaminates gaming chips while in use in a casino.

FIG. 16 illustrates a partial cross section view of gaming chip tray embodiment of the present invention. As illustrated, gaming chip tray 1600 is generally rectangular in shape and often includes a flange 1602 which seats on the gaming table once the lower section 1604 is lowered into place. Gaming chip tray 1600 includes a plurality of semi-circular profile recesses 1606 constructed to receive a plurality of gaming chips 1620. As illustrated gaming chip tray 1600 includes a plurality of semi-circular profile recesses 1606 constructed to receive a plurality of gaming chips 1620 and within each of the plurality of semi-circular profile recesses 1606 is a plurality of openings 1612 that allow for the transmission of light or radiation to pass through from under the top portion of the gaming chip tray 1600. Those skilled in the art will recognize that the openings 1612 can be of many shapes as long as they provide a means of transmission. In addition, some materials may allow for the passage of UV radiation and as such, no openings may be required as long as the UV radiation can reach the gaming chips. During use, gaming chip tray 1600 will be filled with a variety of differing denomination gaming chips such as a $1 chips, $5 chips, $25 chips, $100 chips, etc., arranged for easy counting in the event a dealer must pay a player once they have won a wager. As the table game progresses, the gaming chips routinely go out and then come back for placement in the gaming chip tray 1600 depending on the outcomes of wagering activities. Accordingly, the chips will be exposed to the UV radiation to the extent necessary to reduce or eliminate contamination form viruses and the like. As illustrated, a series of UV or RGB-UV LEDs 1614 are located beneath the upper chip holding section of the gaming chip tray 1600. Placement is such that the UV radiation is allowed to pass through the openings 1612 and radiate the gaming chips, thereby reducing or eliminating the contamination of the gaming chips. Those familiar with the art will recognize that while the contamination of the gaming chips 1620 may only be slightly reduced or even not reduced on a particular placement, the repeated placement and replacement into the gaming chip tray 1600 may be additive to the overall decontamination of the gaming chips 1620. This repeated exposure of objects may occur in many embodiments of the present invention. The series of UV or RGB-UV LEDs 1614 which are located beneath the upper chip holding section of the gaming chip tray 1600 are controlled by controller 1616, as schematically shown, which includes a power supply 1622. As illustrated, the location if the series of UV or RGB-UV LEDs 1614 may also be located above the gaming chip tray 1600 on the underside of cover 1610 as shown in broken line. When this is the case, the gaming chips are decontaminated when the cover is closed or in applications where distribution may be automatically controlled.

Figure 17:
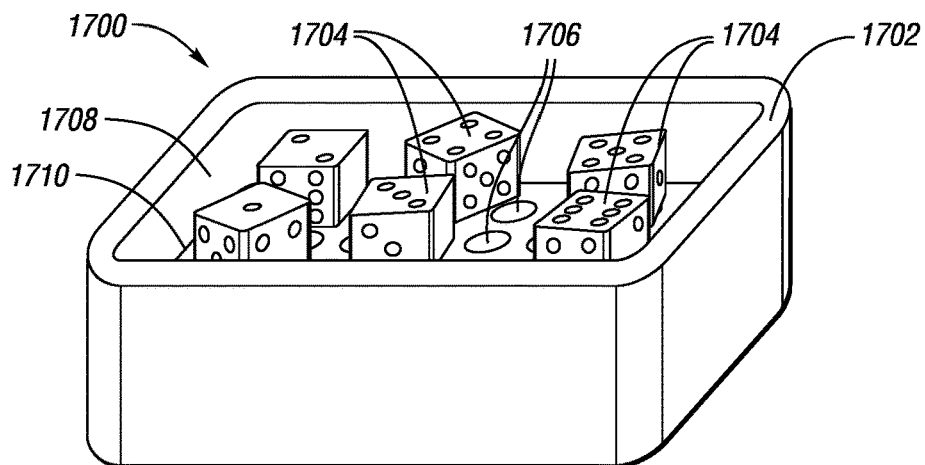
FIG. 17 illustrates an isometric view of a dice holding device embodiment of the present invention which sterilizes, disinfects and decontaminates dice while in use in a casino.

FIG. 17 illustrates an isometric view of a dice holding device embodiment 1700 of the present invention which sterilizes, disinfects and decontaminates dice while in use in a casino. As illustrated the dice holding device housing 1702 includes a rectangular opening 1708 which receives a plurality of dice 1704 which sit on the bottom structure 1710 which includes a plurality of openings 1706. Those skilled in the art will recognize that dice holding device 1700 may also include a cover or lockable cover (not shown). The plurality of openings 1706 are provided to allow for the passage of UV radiation which sterilize, disinfect and decontaminate the dice 1704. Those skilled in the art will recognize that the openings 1706 can be of many shapes as long as they provide a means of transmission of the UV radiation. In addition, some materials may allow for the passage of UV radiation and as such, no openings may be required as long as the UV radiation can reach the gaming dice. Those familiar with the art will recognize that while the contamination of the dice 1704 may only be slightly reduced or even not reduced on a particular placement, the repeated placement and replacement into the dice holding device 1700 may be additive to the overall decontamination of the dice 1704. This repeated exposure of objects may occur in any embodiments of the present invention. The dice holding device 1700 may be permanently mounted to a gaming table, such as a craps table or similar or movable as long movable placement allows for a power supply and controller, if needed.

Figure 18:
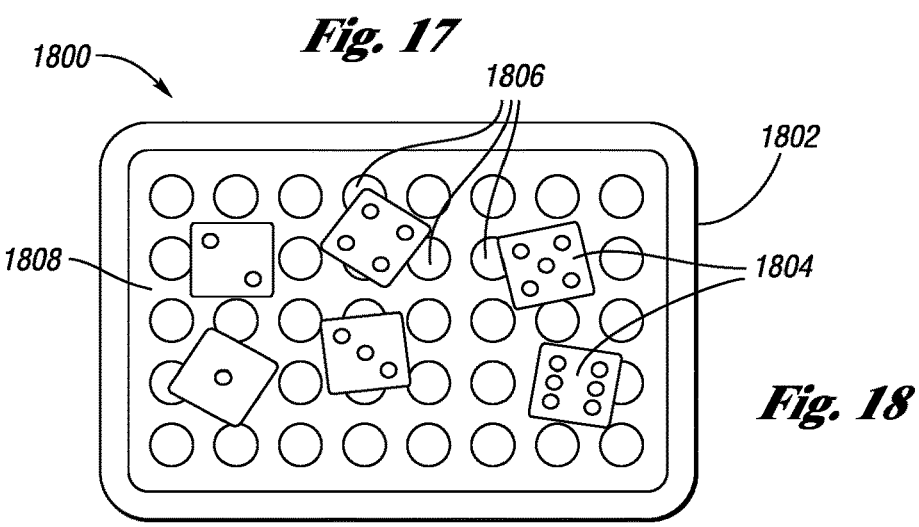
FIG. 18 illustrates a top plan view of the dice holding device embodiment of the present invention as illustrated in FIG. 17 which sterilizes, disinfects and decontaminates dice while in use in a casino.

FIG. 18 illustrates a top plan view of a dice holding device embodiment 1800 of the present invention which sterilize, disinfect and decontaminates dice while in use in a casino. As illustrated the dice holding device housing 1802 includes a generally rectangular opening 1808 which receives a plurality of dice 1804 which sit on the bottom structure 1810 which includes a plurality of openings 1806. The plurality of openings 1806 are provided to allow for the passage of UV radiation which sterilize, disinfect and decontaminate the dice 1804. Those skilled in the art will recognize that the openings 1806 or openings in any embodiment can be of many shapes or materials as long as they provide a means of transmission of the UV radiation. In addition, some materials may allow for the passage of UV radiation and as such, no openings may be required as long as the UV radiation can reach the gaming dice. Those familiar with the art will recognize that while the contamination of the dice 1804 may only be slightly reduced or even not reduced on a particular placement, the repeated placement and replacement into the dice holding device 1800 may be additive to the overall decontamination of the dice 1804. This repeated exposure of objects may occur in any embodiments of the present invention. The dice holding device embodiment 1800 may be permanently mounted to a gaming table, such as a craps table or similar or movable as long as movable placement allows for a power supply and controller, if needed.

Figure 19:
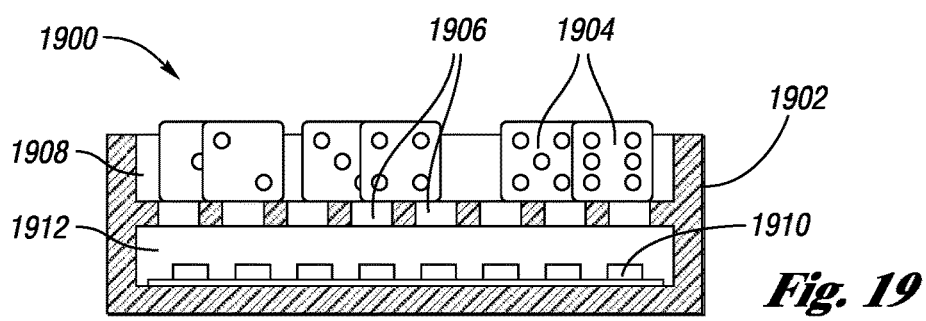
FIG. 19 illustrates a cross section view of dice holding device embodiment of the present invention as illustrated in FIG. 17 which sterilizes, disinfects and decontaminates dice while in use in a casino.

FIG. 19. illustrates cross section view of a dice holding device embodiment 1900 of the present invention which sterilize, disinfect and decontaminates dice while in use in a casino. As illustrated the dice holding device housing 1902 includes a rectangular opening 1908 which receives a plurality of dice 1904 which sit on the bottom structure 1910 which includes a plurality of openings 1906. The plurality of openings 1906 are provided to allow for the passage of UV radiation which sterilize, disinfect and decontaminate the dice 1904. Those skilled in the art will recognize that the openings 1906 can be of many shapes as long as they provide a means of transmission of the UV radiation provided by UV or RGB-UV LEDs 1910 which are located in the opening 1912. In addition, some materials may allow for the passage of UV radiation and as such, no openings may be required as long as the UV radiation can reach the gaming dice. Those familiar with the art will recognize that while the contamination of the dice 1904 may only be slightly reduced or even not reduced on a particular placement, the repeated placement and replacement into the dice holding device 1900 may be additive to the overall decontamination of the dice 1904. This repeated exposure of objects may occur in any embodiments of the present invention. The dice holding device 1900 may be permanently mounted to a gaming table, such as a craps table or similar or movable as long as movable placement allows for a power supply and controller, if needed.

Figure 20:
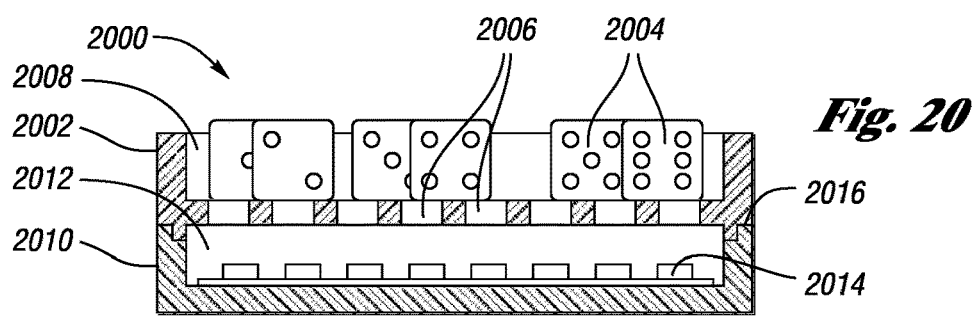
FIG. 20 illustrates another dice holding device embodiment of the present invention which sterilizes, disinfects and decontaminates dice while in use in a casino.

FIG. 20 illustrates cross section view of another dice holding device 2000 of the present invention which sterilize, disinfect and decontaminates dice while in use in a casino. As illustrated the dice holding device housing 2002 has a two-piece construction and includes a rectangular opening 2008 which receives a plurality of dice 2004 which sit on the bottom structure 2010 which includes a plurality of openings 2006. These structures in turn are mounted to a bottom section 2010 which interlocks with the top section 2002 through the step relationship of the construction 2016. The plurality of openings 2006 are provided to allow for the passage of UV radiation which sterilize, disinfect and decontaminate the dice 2004. Those skilled in the art will recognize that the openings 2006 can be of many shapes as long as they provide a means of transmission of the UV radiation provided by UV or RGB-UV LEDs 2014 which are located in the opening 2012. In addition, some materials may allow for the passage of UV radiation and as such, no openings may be required as long as the UV radiation can reach the gaming dice. Those familiar with the art will recognize that while the contamination of the dice 2004 may only be slightly reduced or even not reduced on a particular placement, the repeated placement and replacement into the dice holding device 2000 may be additive to the overall decontamination of the dice 2004. This repeated exposure of objects may occur in any embodiments of the present invention. The dice holding device embodiment 2000 may be permanently mounted to a gaming table, such as a craps table or similar or movable as long as movable placement allows for a power supply and controller, if needed. In addition, the upper portion 2002 which holds the dice 2004 is removable and can be passed to a dealer or player separately from the lower base portion 2010.

Figure 21:
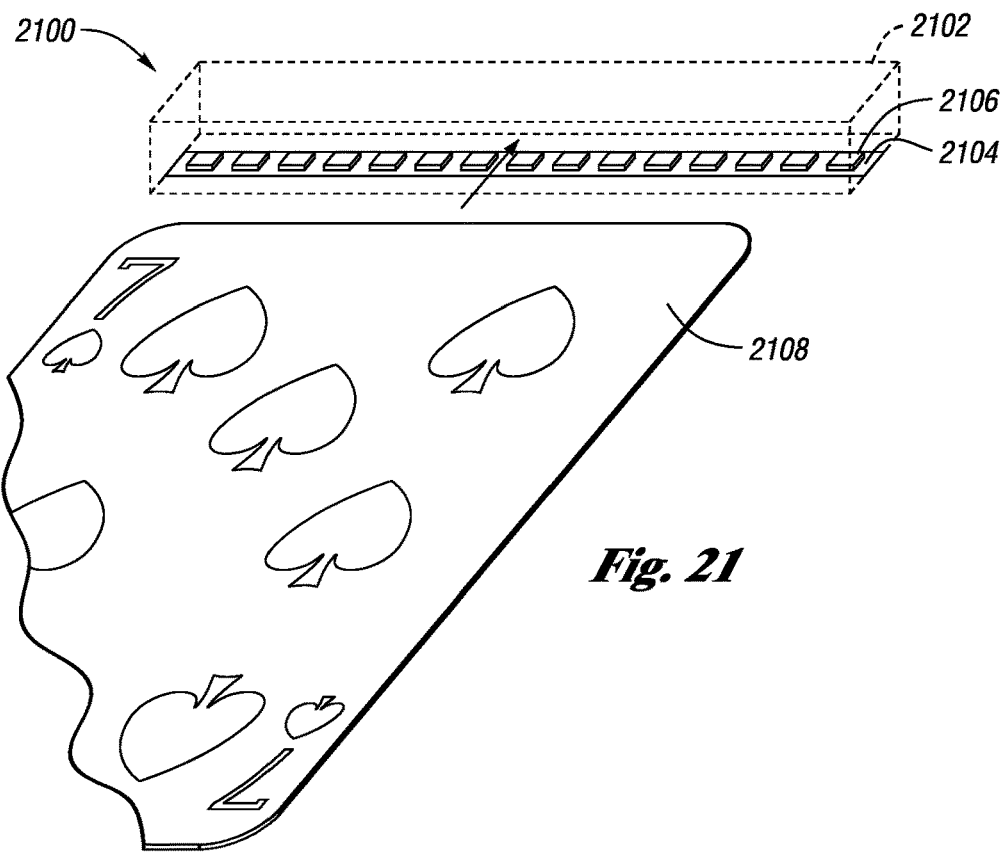
FIG. 21 illustrates a pass-through sterilization, disinfection and decontamination station embodiment used for playing cards and the like which is incorporated into an automatic card shuffler, an automatic playing card shoe, and similar devices.

FIG. 21 illustrates a pass-through sterilization, disinfection and decontamination station embodiment used for playing cards and the like which may be incorporated into an automatic card shuffler, an automatic playing card shoe, and similar devices. As illustrated, the pass-through sterilization, disinfection and decontamination station 2100 includes a housing 2102 shown in broken line which houses an LED strips 2104 located on one plane, the LED strip 2104 includes a plurality of UV or RGB-UV LEDs 2106. In operation, playing cards 2108 pass through the pass-through sterilization, disinfection and decontamination station to reduce or eliminate viruses and the like. Those skilled in the art will recognize that any of the pass-through sterilization, disinfection and decontamination station embodiments may be utilized to sterilize, disinfect and decontaminate any infected or potentially infected object.

Figure 22:
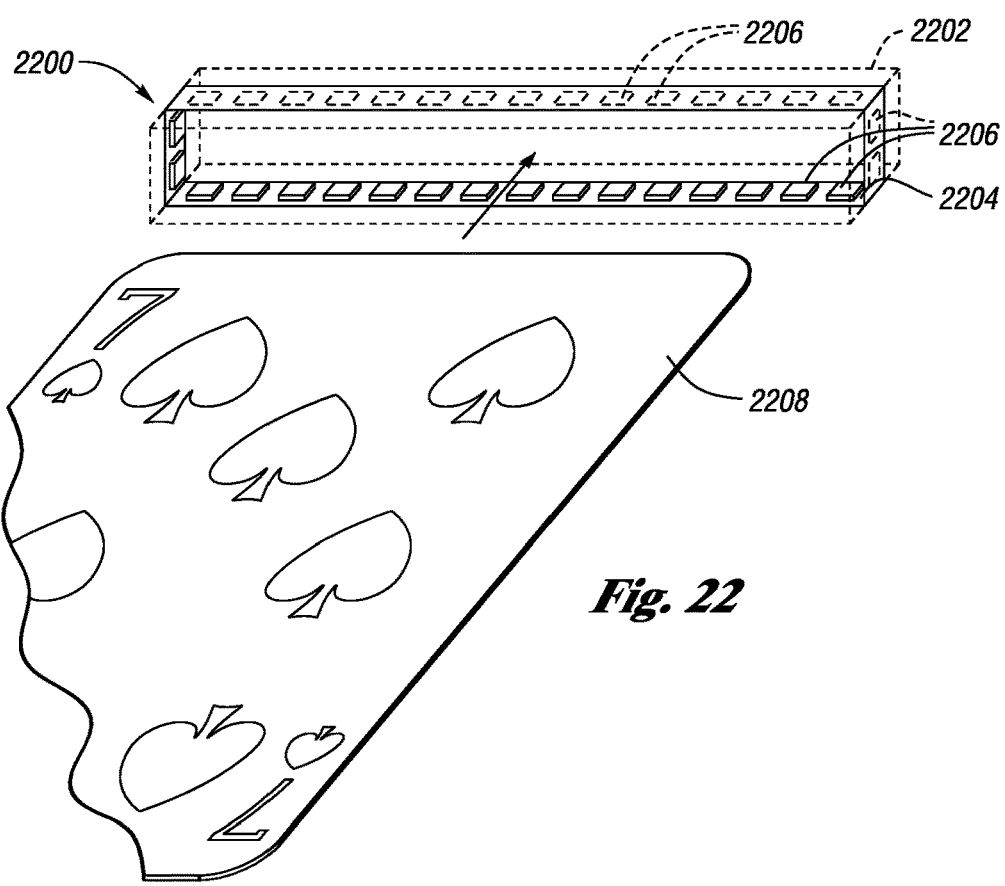
FIG. 22 illustrates another pass-through sterilization, disinfection and decontamination station embodiment used for playing cards and the like which is incorporated into an automatic card shuffler, an automatic playing card shoes, and similar devices.

FIG. 22 illustrates another pass-through sterilization, disinfection and decontamination station embodiment used for playing cards and the like which may be incorporated into an automatic card shuffler, an automatic playing card shoe, and similar devices. As illustrated, the pass-through sterilization, disinfection and decontamination station 2200 includes a housing 2202 shown in broken line which houses LED strips 2204 located on multiple planes, each with a plurality of UV or RGB-UV LEDs 2206. In operation, playing cards 2208 pass through the pass-through sterilization, disinfection and decontamination station to reduce or eliminate viruses and the like.

Figure 23:
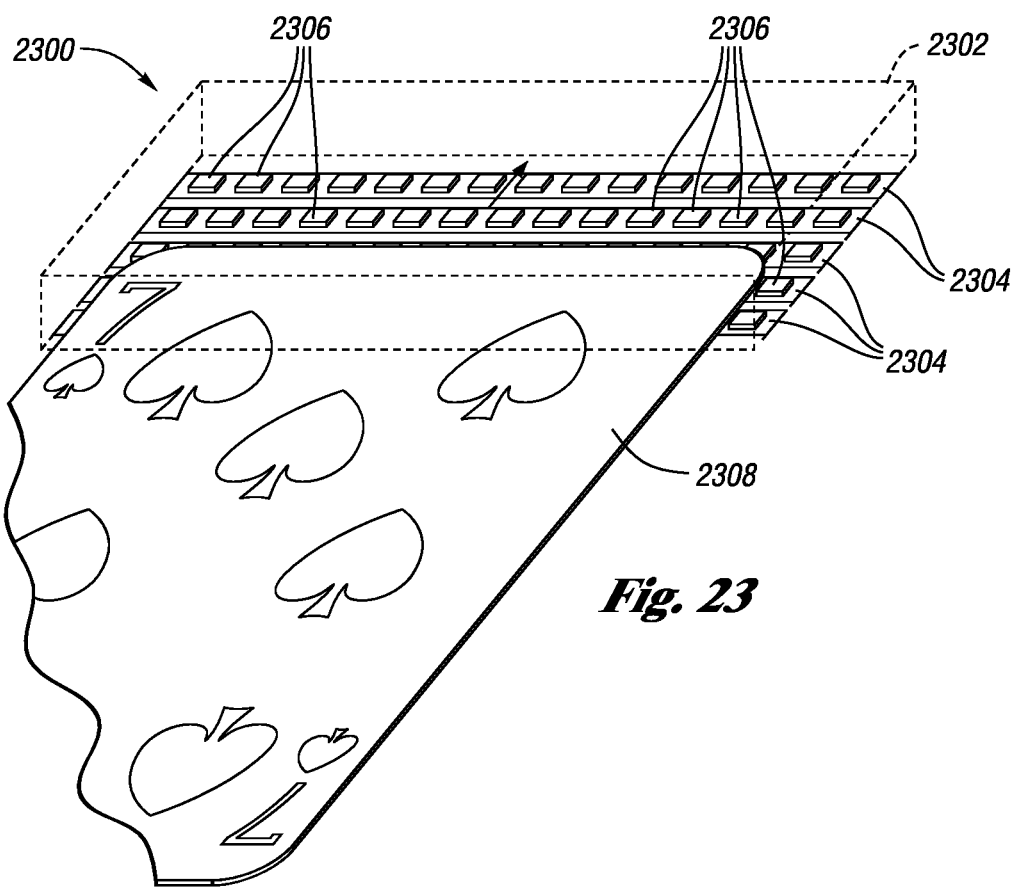
FIG. 23 illustrates another pass-through sterilization, disinfection and decontamination station embodiment used for playing cards and the like which is incorporated into an automatic card shuffler, an automatic playing card shoe, and similar devices.

FIG. 23 illustrates another pass-through sterilization, disinfection and decontamination station embodiment used for playing cards and the like which may be incorporated into an automatic card shuffler, an automatic playing card shoe, and similar devices. As illustrated, the pass-through sterilization, disinfection and decontamination station 2300 includes a housing 2302 shown in broken line which housed a plurality of LED strips 2304 located on one plane, each with a plurality of UV or RGB-UV LEDs 2306. In this embodiment, the LED strips 2304 are placed side-by-side. In operation, playing cards 2308 pass through the pass-through sterilization, disinfection and decontamination station to reduce or eliminate viruses and the like.

Figure 24:
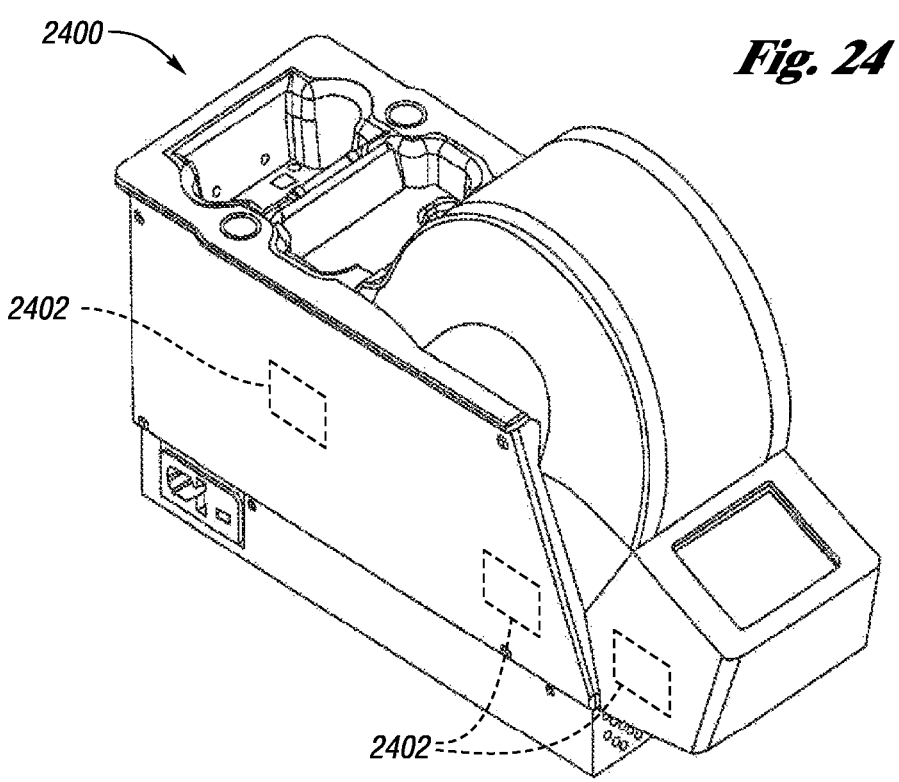
FIG. 24 illustrates a typical prior art automatic playing card shuffler of which there are many types and styles.

FIG. 24 illustrates a typical prior art automatic playing card shuffler 2400 of which there are many types and styles, includes mechanisms for playing card distribution such as manual or automatic playing cards shoes. As shown in broken line, a pass-through sterilization, disinfection and decontamination station or stations may be located in any convenient and effective location 2402 within the automatic playing card shuffler 2400.

Figure 25:
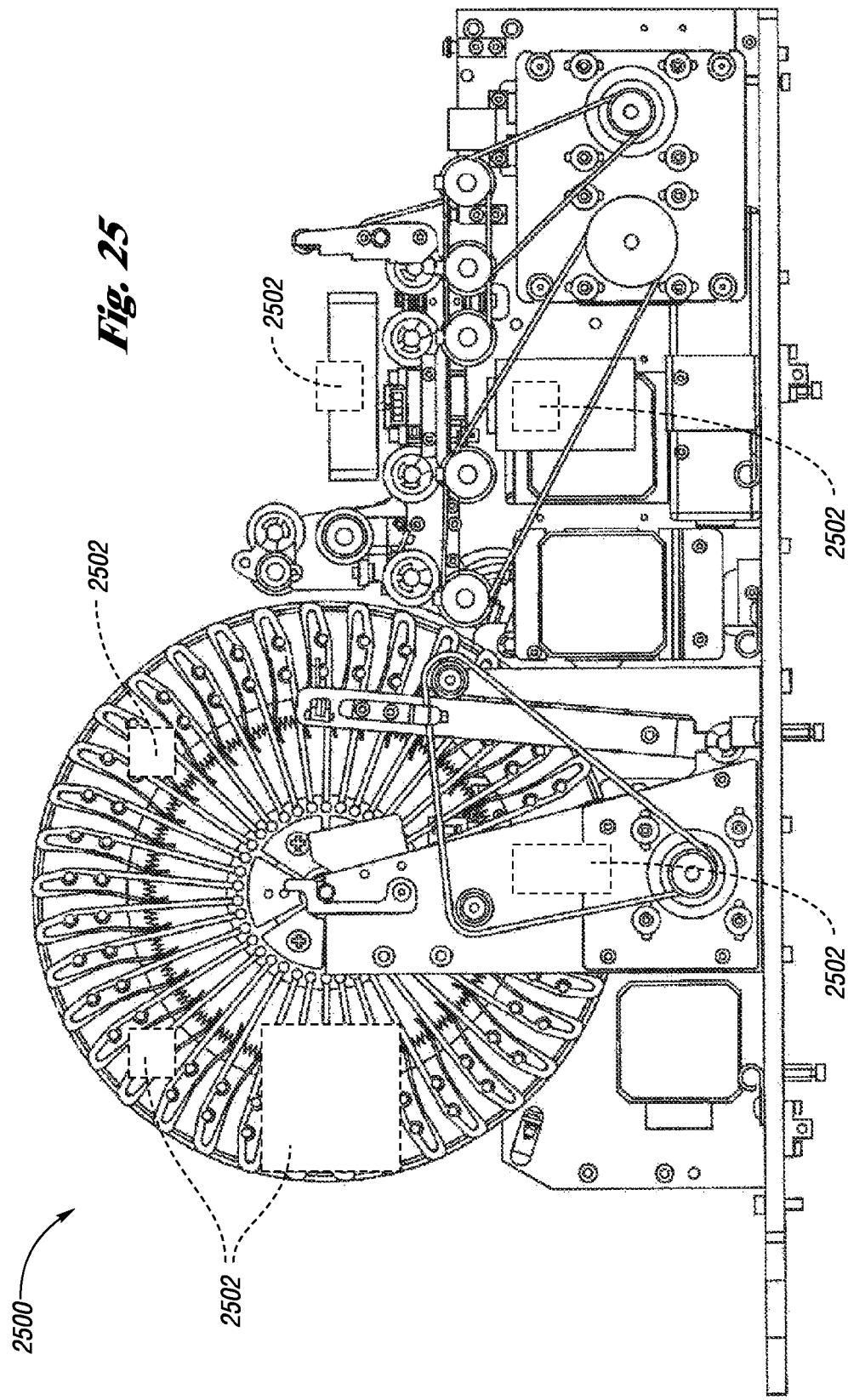
FIG. 25 illustrates side elevational view a typical prior art automatic playing card shuffler with the cover or housing removed, of which there are many types and styles.

FIG. 25 illustrates side elevational view a typical prior art automatic playing card shuffler 2500 with the cover or housing removed, of which there are many types and styles. As illustrated with broken lines, pass-through sterilization, disinfection and decontamination station(s) may be located in any convenient area of the playing card shuffler 2500. Those skilled in the art will recognize that some redesign of any device incorporating a pass-through sterilization, disinfection and decontamination station embodiment may be necessary to allow for the pass-through sterilization, disinfection and decontamination stations 2502. In this embodiment, either the rectangular opening pass-through sterilization and decontamination station(s) or a single or plurality of planar sterilization, disinfection and decontamination station(s), similar to that illustrated in FIG. 23, may be utilized. In many scenarios, it is possible to irradiate the entire or a large portion of the interior of such mechanisms for maximum effectiveness.

While automatic playing card shufflers have been described in detail, the same principles and scope apply to currency counting devices, automatic teller machines, etc., whereas, instead of playing cards being processed, currency is processed. Similarly, other gaming devices or peripheral devices may also be equipped with embodiments of the present invention. These devices include but are not limited to magnetic card reads, TITO printers, bill validators, etc.

While many of the embodiments set forth above detail the use of openings allowing the passage of UV radiation to contact the objects (e.g., chips, dice and cards) to be sterilized and decontaminated, those skilled in the art will recognize that the openings may be replaced with, or modified to, include translucent materials, such as glass and/or plexiglass, that permit the passage of UV radiation. By way of example, the plurality of openings 1512 shown in the chip tray 1500 of FIG. 15 may be covered with a translucent material or more appropriately the semi-circular profile recesses 1506 may be constructed of a translucent material obviating the need for separate openings 1512. Alternatively, the translucent material may also incorporate openings.

In one embodiment, the button deck buttons and other EGM features may be fabricated of translucent materials which allow the passage of UV light such that the UV light sources may be built into or installed into the button deck housing. In this manner, the sterilization, disinfection and/or decontamination of the buttons and other EGM features is done from within the EGM as opposed to via attachments of the sterilization, disinfection and decontamination mechanisms 150 on the external surface of the EGM cabinet or deck.

Figure 26:
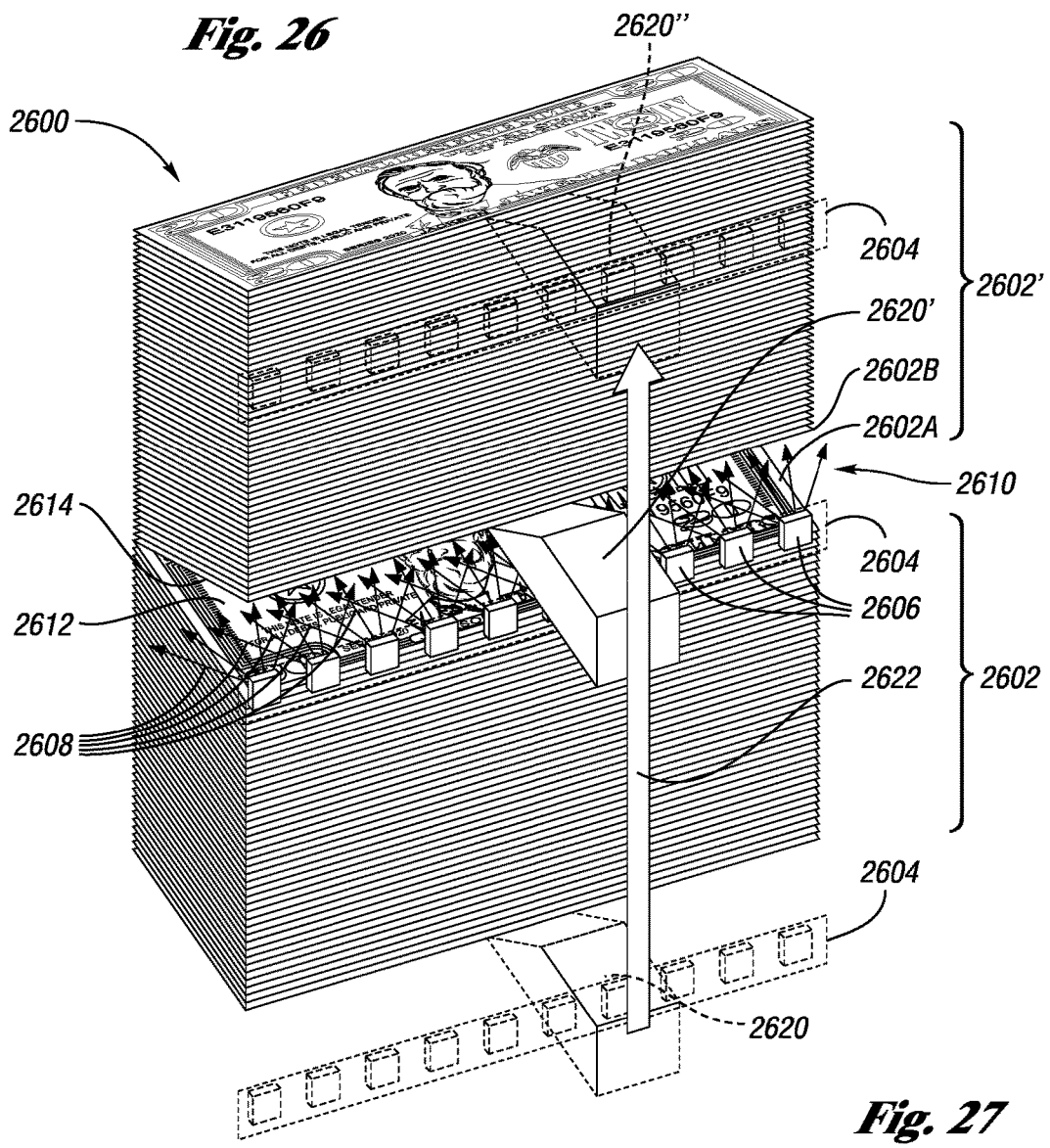
FIG. 26 illustrates a stack separator mechanism according to the embodiments of the present invention.

FIG. 26 illustrates a stack separator mechanism 2600 according to embodiments of the present invention which separates stacked items such as currency 2602 or similar items such as playing cards, gaming chips, or the like in devices and mechanisms such as automatic teller machines, EGM bill acceptors, currency counting machines, card shufflers, gaming chip trays, playing card shoes, manual or automated table games cash drop boxes, and the like. Generally, items are stacked on top of one another as shown in currency stack 2602. Those skilled in the art will recognize the stacked items need not be stacked vertically as items may be stacked horizontally or in any convenient angular relationship. Stacked items may limit or prohibit the effective use the embodiments of the present invention as there is little or no room between stacked items resulting in the inability for UV radiation to reach the top or bottom surfaces of the stacked items such as currency 2602, playing cards, or the like. The stack separator mechanism 2600 provides for on opening between stacked items 2602 and 2602' (and 2602") that allows for the UV radiation to reach the top surface 2612 and bottom surface 2614 of the stacked items 2602 via use of a stack separator block 2620. Typically, the stack separator block 2620 will move in a parallel fashion with the stacked items 2602, starting from the bottom of the stacked items 2602. Those skilled in the art will recognize that the stack separator block 2620 may be movable in any convenient direction as long as it results in adequate separation of the stacked items. As shown, a stack separator block 2620 starts at the bottom of stacked items 2602 and is placed slightly under the stacked items 2602. As the stack separator block 2620' moves upwardly as shown by direction arrow 2622, it incrementally lifts the stacked items 2602' upwardly to provide a separation 2610, revealing surfaces 2612 and 2614. The separation 2610 allows for UV radiation 2608, provided by UV LED strip 2604 and UV LEDs 2606, to reach surfaces 2612 and 2614. The UV strip 2604 and UV LEDs 2606 may move with stack separator block 2620 or remain stationary. In a stationary embodiment, a plurality of LED strips 2604 may be employed to allow for a more complete exposure to the UV radiation. As the stack separator block moves, it may move upwardly just enough to release the top stacked item 2602A therefore providing a new separation 2610 for the stacked item 2602B directly above the previous stacked item 2602A. Movement of stack separator block 2620, may be incremental or indexed where the stack separator block 2620 moves a distance to reveal the next set of separated items and then stop to allow for prolonged exposure to the UV radiation 2608. Preferably the movement distance is about that of the item or currency thickness. Alternatively, stack separator block may have continuous movement from bottom to top, retract, return to the original bottom location and extend and then repeat as often as desired, similar to paging through a book, over and over. Accordingly, utilizing the stack separator mechanism 2600 will allow for sterilization, disinfecting and decontaminating of the entire stack of items, either partially or fully. Those skilled in the art will recognize that while a mechanical mechanism is illustrated, similar separating means such as utilizing air pressure mechanisms, rollers, stacker wheels, etc., may be employed to provide similar separation of stacked items.

Figure 27:
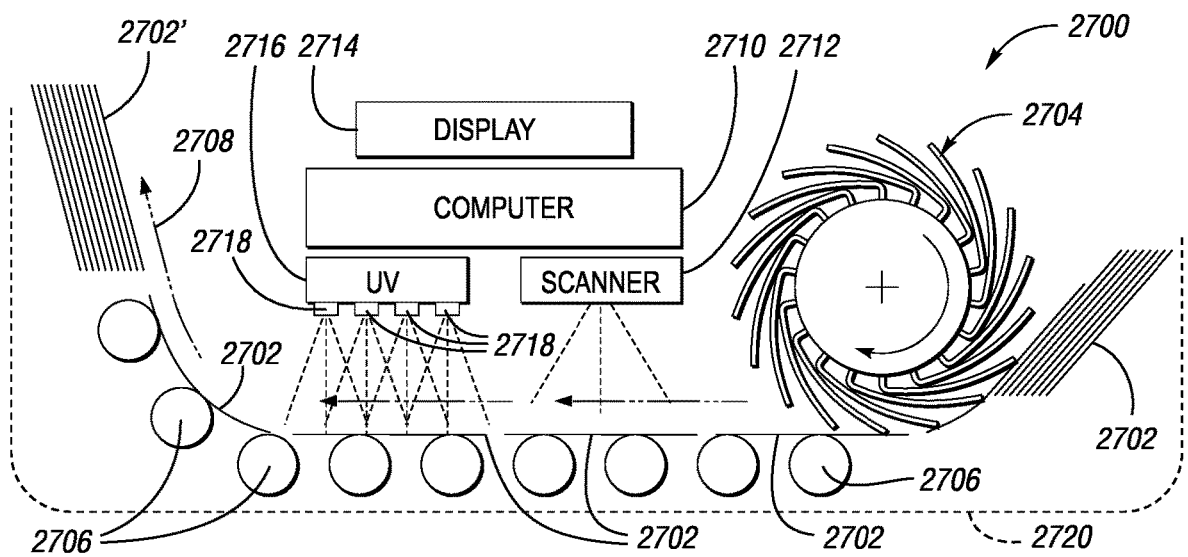
FIG. 27 illustrates a schematic side view of a currency counting device according to the embodiments of the present invention.

FIG. 27 illustrates a schematic side view of a currency counting device 2700 embodiment of the present invention. Currency is loaded as a stack of currency 2702. During operation, stacker wheel 2704 rotates to pull the top item into the currency counting device 2700. The currency items 2702 then proceed individually through the various stations of currency counting device 2700 as shown by arrows 2708 through use of rollers 2706 or similar means as schematically illustrated. As the items moves through the currency counting device 2700, it is scanned by scanner 2712 to determine the currency denomination, number of items, determination of counterfeit items, etc. Scanner 2712 is controlled by computer 2710 which also operates display 2714 which may show total dollar amount, number of currency items, number of counterfeit items (if applicable), etc. Computer 2710 may also be in communication with additional computers for accounting and other purposes. As the currency item proceeds through the currency counting device 2700, it is exposed to the UV radiation station 2716 and UV LEDs 2718 for sterilization, disinfecting and decontaminating. Typically, the UV radiations station will expose little or no radiation outside of the currency counting device 2700 as it is contained within housing 2720 allowing for increased intensity for more rapid processing. Following scanning and UV radiation, the currency items will leave the processing and transfer area of the currency counting device 2700 and be stacked as shown 2702'. Those skilled in the art will recognize that the sequence of stations or operations may be in any convenient order. Moreover, those skilled in the art will recognize that the principles of the various UV sterilization, disinfecting and decontaminating embodiments may apply to any type or design currency counting device.

Figure 28:
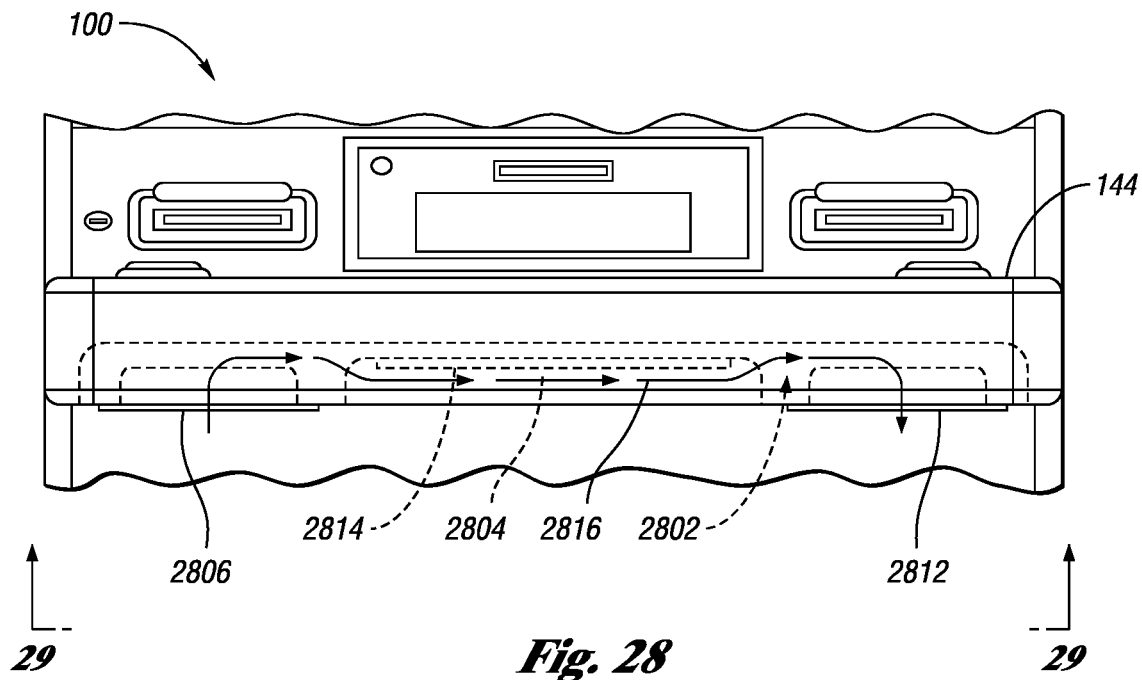
FIG. 28 illustrates a front elevation view of the button deck area of the EGM of FIG. 1 with an air purification system according to the embodiments of the present invention.

FIG. 28 illustrates a broken away front elevation view of the button deck area of the EGM of FIG. 1 with another embodiment of the present invention incorporating an UV air purification system 2802. As illustrated, preferably the UV air purification system 2802 is located below the button deck 144 of the EGM 100. The UV air purification system 2802 includes an air purification chamber 2804 within UV air purification system 2802. Within the air purification chamber 2804, one or more UV lighting elements 2814 are located. Air is brought into the air purification chamber 2804 via intake 2806 and then treated in air purification chamber 2804 and then forced out via the exhaust mechanism 2812, after processing as illustrated by air flow arrows 2816. The UV air purification system 2802 may operate at all times, may be operator controlled or timed via the EGM administrative settings, or turned on or off by a player, for example. Those skilled in the art will recognize that while two separate fans are illustrated in FIG. 28, a single individual fan may also be utilized to serve both intake and exhaust functions. Those skilled in the art will recognize that while the UV air purification system 2802 is illustrated as located underneath the button deck 144, it may be located in other areas of the EGM 100 such as the lower support structure of the EGM 100, above the display or any other convenient location.

Figure 29:
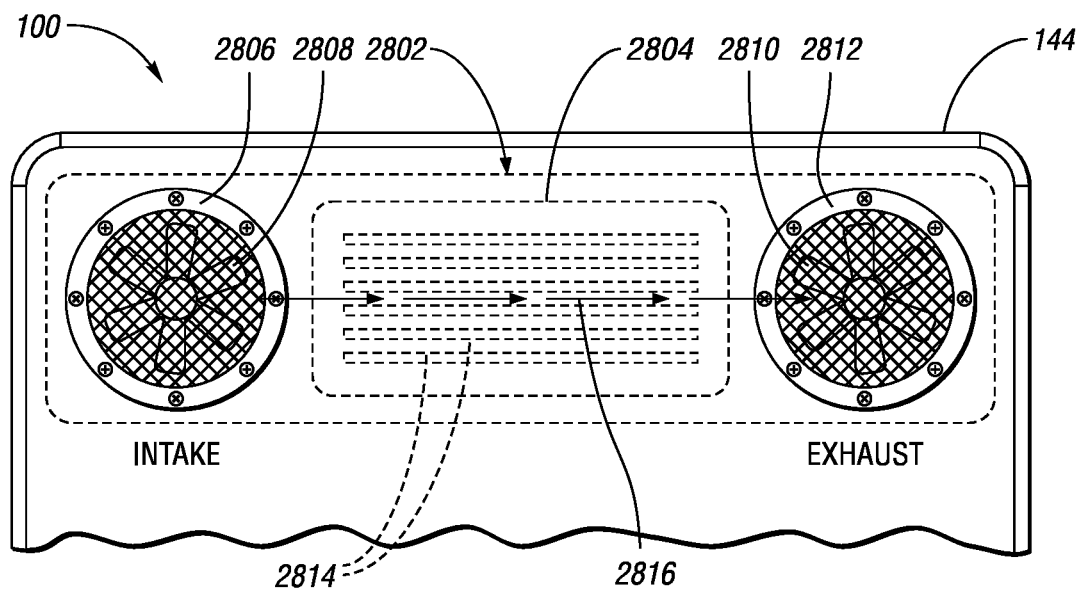
FIG. 29 illustrates a bottom plan view of the EGM of FIG. 1 with an air purification system according to the embodiments of the present invention.

FIG. 29 illustrates a partial bottom plan view of the button deck area of the EGM 100 of FIG. 1 with incorporating an UV air purification system 2802. As illustrated, the UV air purification system 2802 may be located below the button deck 144 of the EGM 100. The UV air purification system 2802 includes an air purification chamber 2804 within UV air purification system 2802. Within the air purification chamber 2804, one or more UV lighting elements 2814 are located. Air is brought into the air purification chamber 2804 via intake 2806 via fan 2808 and treated in air purification chamber 2804 and then forced out via the fan 2810 of exhaust mechanism 2812, after processing as illustrated by air flow arrows 2816. The UV air purification system 2802 may operate at all times, may be operator controlled or timed via the EGM administrative settings, or turned on or off by a player. Those skilled in the art will recognize that while two separate fans are illustrated in FIG. 28, an individual fan may also be utilized to serve both intake and exhaust functions. Those skilled in the art will recognize that while the UV air purification system 2802 is illustrated as located underneath the button deck 144, it may be located in other areas of the EGM 100 such as the lower support structure of the EGM 100, above the display or any other convenient location.

In another embodiment, the UV air purification system 2602 may incorporate a filter near exhaust mechanism 2612. In one embodiment, the filter is saturated with one or more agents (e.g., alcohol, sanitizer, etc.) known to reduce or kill viruses of the type the system herein is designed to control. For example, the air leaving the UV air purification system 2602 must pass through the filter before or after encountering fan 2610. In one embodiment, the blades of the fan 2610 may incorporate saturated filters for reducing or killing viruses.

Although the invention has been described in detail with reference to several embodiments, additional variations and modifications exist within the scope and spirit of the invention as described and defined in the following claims.

We claim:

1. A magnetic stripe card disinfecting device comprising:
   a housing;
   one or more mechanisms contained within said housing, said one or more mechanisms configured to receive, transport, eject and/or stack one or more magnetic stripe cards;
   a magnetic stripe card reader, writer or combination magnetic stripe card reader and writer; and
   one or more magnetic stripe card disinfecting mechanisms configured to at least partially separate individual magnetic stripe cards while in a stacked arrangement, a source of ultraviolet light positioned proximate to said one or more mechanisms, said source of ultraviolet light configured to transmit ultraviolet light onto at least a portion of said front and back surfaces of said magnetic stripe cards when said one or more magnetic stripe cards are separated by said one or more magnetic stripe card disinfecting mechanisms, said source of ultraviolet light capable of, and configured, via time and/or intensity, to at least partially sterilize, disinfect and/or decontaminate at least a portion of said front and back surfaces of said one or more magnetic stripe cards.

2. The magnetic stripe card disinfecting device of claim 1 wherein the source of ultraviolet light is one or more UVC LEDs with a wavelength between about 100 nm and 280 nm.

3. The magnetic stripe card disinfecting device of claim 1 further comprising one or more reflectors and/or directors to generally direct ultraviolet light produced by said source of ultraviolet light on said front and back surfaces of said one or more magnetic stripe cards as said one or more magnetic stripe cards are received, passed through, ejected, and/or stacked by said one or more mechanisms.

4. The magnetic stripe card disinfecting device of claim 1 wherein said one or more magnetic stripe card separator mechanisms are configured to move in a generally vertical fashion and at least partially separate pairs of neighboring individual magnetic stripe cards while in a stacked arrangement so that UV light can be directed onto the front and back surfaces of individual magnetic stripe cards within said stacked arrangement.

5. The magnetic stripe card disinfecting device of claim 4 wherein said one or more magnetic stripe card separator mechanisms are configured to disengage from separating said magnetic stripe cards in a stacked arrangement and return to a predetermined vertical position once reaching a predetermined upper generally vertical travel position.

6. The magnetic stripe card disinfecting device of claim 1 wherein the source of the ultraviolet light is mounted to the exterior of the housing and transmits ultraviolet light onto said front and back surfaces of said one or more magnetic stripe cards.

7. A magnetic stripe card disinfecting device comprising;
a housing;
a magnetic stripe card reader, writer or combination magnetic stripe card reader and writer;
a magnetic stripe card input section and a magnetic stripe card output section;
one or more mechanisms for moving one or more magnetic stripe cards from a first position within said housing to said magnetic stripe card output section;
one or more magnetic stripe card separator mechanisms configured to at least partially separate individual magnetic stripe cards while in a stacked arrangement;
and a source of ultraviolet light positioned proximate to said magnetic stripe card input section, said source of ultraviolet light configured to transmit ultraviolet light onto the front and back surfaces of said one or more magnetic stripe cards as said one or more magnetic stripe cards are separated by said one or more magnetic stripe card separator mechanisms, said source of ultraviolet light capable of, and configured, via time and/or intensity, to at least partially sterilize, disinfect and/or decontaminate at least a portion of said front and back surfaces of said one or more magnetic stripe cards.

8. The magnetic stripe card disinfecting device of claim 7 wherein the source of ultraviolet light is one or more UVC LEDs with a wavelength between about 100 nm and 280 nm.

9. The magnetic stripe card disinfecting device of claim 7 further comprising one or more reflectors and/or directors to generally direct ultraviolet light produced by said source of ultraviolet light on said front and back surfaces of said one or more magnetic stripe cards as said one or more magnetic stripe cards are moved from said magnetic stripe card input section and/or moved to said magnetic stripe card output section.

10. The magnetic stripe card disinfecting device of claim 7 wherein said one or more card separator mechanisms are configured to move in a generally vertical fashion and at least partially separate pairs of neighboring individual magnetic stripe cards while in a stacked arrangement so that UV light can be directed onto the front and back surfaces of each of said individual magnetic stripe cards within said stacked arrangement.

11. The magnetic stripe card disinfecting device of claim 10 wherein said one or more magnetic stripe card separator mechanisms are configured to disengage from separating said magnetic stripe cards in a stacked arrangement and return to a predetermined position once reaching a predetermined upper generally vertical travel position.

12. The magnetic stripe card disinfecting device of claim 7 wherein the source of the ultraviolet light is mounted to the exterior of the housing and transmits ultraviolet light onto said front and back surfaces of said one or more magnetic stripe cards.

13. A magnetic stripe card disinfecting device comprising:
a housing having a card input section;
a magnetic stripe card reader, writer or combination magnetic stripe card reader and writer;
one or more mechanisms contained within said housing, said one or more mechanisms configured to receive a plurality of magnetic stripe cards placed in said magnetic stripe card input section;
and one or more magnetic stripe card separator mechanisms configured to at least partially separate individual magnetic stripe cards while in a stacked arrangement so that UV light is capable of, and configured, via time and/or intensity, to at least partially sterilize, disinfect and/or decontaminate at least a portion of each of said plurality of magnetic stripe cards.

14. The magnetic stripe card disinfecting device of claim 13 wherein the source of ultraviolet light is one or more UVC LEDs with a wavelength between about 100 nm and 280 nm.

15. The magnetic stripe card disinfecting device of claim 13 further comprising one or more reflectors and/or directors to generally direct ultraviolet light produced by said source of ultraviolet light on said front and back surfaces of said magnetic stripe cards as said magnetic stripe cards are at least partially separated by said one or more magnetic stripe card separator mechanisms.

16. The magnetic stripe card disinfecting device of claim 13 wherein said one or more magnetic stripe card separator mechanisms are configured to move in a generally vertical fashion and at least partially separate pairs of neighboring individual magnetic stripe cards.

17. The magnetic stripe card disinfecting device of claim 16 wherein said one or more magnetic stripe card separator mechanisms are configured to disengage from separating said magnetic stripe cards in a stacked arrangement and return to a predetermined position once reaching a predetermined upper generally vertical travel position.

18. The magnetic stripe card disinfecting device of claim 13 wherein the source of the ultraviolet light is mounted to the exterior of the housing and transmits ultraviolet light onto said front and back surfaces of magnetic stripe cards.

19. A method of at least partially sterilizing, disinfecting and/or decontaminating front and back surfaces of one or more magnetic stripe cards while using a magnetic stripe card reader, writer or combination magnetic stripe card reader and writer comprising:
(i) configuring said magnetic stripe card reader, writer or combination magnetic stripe card reader and writer device to receive, at a magnetic stripe card input area, one or more magnetic stripe cards; (ii) configuring said magnetic stripe card reader, writer or combination magnetic stripe card reader and writer device to move said received magnetic stripe cards from said input area to a magnetic stripe card output area; (iii) configuring one or more magnetic stripe card separator mechanisms to at least partially separate individual magnetic stripe cards while in a stacked arrangement and (iv) utilizing a source of ultraviolet light to transmit ultraviolet light on the front and back surfaces of individual magnetic stripe cards while said one or more magnetic stripe card separator mechanisms separate individual magnetic stripe cards within said stacked arrangement, said UV light capable of, and configured, via time and/or intensity to at least partially sterilize, disinfect and/or decontaminate at least a portion of said one or more magnetic stripe cards after said one or more magnetic stripe cards are received at said magnetic stripe card input area and before said one or more magnetic stripe cards are removed from said magnetic stripe card output area.

20. The method of claim 19 further comprising utilizing a source of ultraviolet light to transmit ultraviolet light onto said front and back surfaces of said magnetic stripe cards as said one or more magnetic stripe cards are moved from said magnetic card strip input area to said magnetic card stripe output area.

21. The method of claim 19 further comprising utilizing one or more UVC LEDs with a wavelength between about 100 nm and 280 nm as said source of ultraviolet light.

22. The method of claim 19 further comprising utilizing one or more reflectors and/or directors to generally direct ultraviolet light produced by said source of ultraviolet light on said front and back surfaces of said one or more magnetic stripe cards after said one or more magnetic stripe cards are received in at said magnetic stripe card input area and before said magnetic stripe cards are removed from said magnetic stripe card output area.

23. The method of claim 19 further comprising moving said one or more magnetic stripe card separator mechanisms in a generally vertical fashion and at least partially separating each pair of neighboring individual magnetic stripe cards while in a stacked arrangement so that UV light can be directed on the front and back surfaces of each individual magnetic stripe cards within said stacked arrangement.

24. The method of claim 19 further comprising moving said one or more magnetic stripe card separator mechanisms in a generally vertical fashion and returning to a predetermined lower vertical position once reaching a predetermined upper vertical position.

25. The method of claim 19 further comprising mounting the source of the ultraviolet light to the exterior of the housing.

26. The method of claim 19 further comprising mounting said one or more magnetic stripe card separator mechanisms near said magnetic stripe card input area.

27. The method of claim 19 further comprising mounting said one or more magnetic stripe card separator mechanisms near said magnetic stripe card output area.

* * * * *